(12) United States Patent
Yoshimoto et al.

(10) Patent No.: US 11,492,398 B2
(45) Date of Patent: Nov. 8, 2022

(54) IL-33 ANTAGONIST-CONTAINING THERAPEUTIC AGENT FOR ENDOMETRIOSIS

(71) Applicants: MITSUBISHI TANABE PHARMA CORPORATION, Osaka (JP); HYOGO COLLEGE OF MEDICINE, Nishinomiya (JP)

(72) Inventors: Tomohiro Yoshimoto, Nishinomiya (JP); Joseph M. Palumbo, Jersey City, NJ (US); Violetta I. Stone, Lebanon, NJ (US); Toru Kato, Nishinomiya (JP); Koubun Yasuda, Nishinomiya (JP)

(73) Assignees: MITSUBISHI TANABE PHARMA CORPORATION, Osaka (JP); HYOGO COLLEGE OF MEDICINE, Nishinomiya (JP)

( * ) Notice: Subject to any disclaimer, the term of this patent is extended or adjusted under 35 U.S.C. 154(b) by 0 days.

(21) Appl. No.: 16/643,502

(22) PCT Filed: Aug. 31, 2018

(86) PCT No.: PCT/JP2018/032494
§ 371 (c)(1),
(2) Date: Feb. 28, 2020

(87) PCT Pub. No.: WO2019/045075
PCT Pub. Date: Mar. 7, 2019

(65) Prior Publication Data
US 2020/0190182 A1 Jun. 18, 2020

Related U.S. Application Data

(60) Provisional application No. 62/552,594, filed on Aug. 31, 2017.

(51) Int. Cl.
*C07K 16/24* (2006.01)
*A61K 39/395* (2006.01)
*A61K 38/17* (2006.01)

(52) U.S. Cl.
CPC .......... *C07K 16/244* (2013.01); *A61K 39/395* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 9,758,578 B2 | 9/2017 | Fujino et al. | |
| 2008/0063634 A1 | 3/2008 | Salfeld et al. | |
| 2014/0099280 A1 | 4/2014 | Girard et al. | |
| 2014/0271658 A1* | 9/2014 | Murphy | A61P 25/00 424/142.1 |
| 2016/0289322 A1 | 10/2016 | Fujino | |
| 2019/0330329 A1 | 10/2019 | Yasuhiro et al. | |
| 2022/0041709 A1 | 2/2022 | Ikemoto et al. | |

FOREIGN PATENT DOCUMENTS

| | | |
|---|---|---|
| CN | 101189265 A | 5/2008 |
| EA | 201591331 A1 | 1/2016 |
| EP | 3 277 717 A1 | 2/2018 |
| JP | 2007-523089 A | 8/2007 |
| JP | 2007-537702 A | 12/2007 |
| JP | 2008-520684 A | 6/2008 |
| JP | 2008-543340 A | 12/2008 |
| JP | 2010-513306 A | 4/2010 |
| JP | 2011-526591 A | 10/2011 |
| JP | 2012-010702 A | 1/2012 |
| JP | 2012-502967 A | 2/2012 |
| JP | 2017-008003 A | 1/2017 |
| WO | WO 2005/007699 A2 | 1/2005 |
| WO | WO 2005/079844 A2 | 9/2005 |
| WO | WO 2006/055638 A2 | 5/2006 |
| WO | WO 2006/128690 A1 | 12/2006 |
| WO | WO 2007/002261 A2 | 1/2007 |
| WO | WO 2008/074004 A2 | 6/2008 |
| WO | WO 2008/132709 A1 | 11/2008 |
| WO | WO 2008/144610 A1 | 11/2008 |
| WO | WO 2010/000721 A1 | 1/2010 |
| WO | WO 2010/032061 A1 | 3/2010 |
| WO | WO 2011/031600 A1 | 3/2011 |
| WO | WO 2012/113927 A1 | 8/2012 |
| WO | WO 2014/152195 A1 | 9/2014 |
| WO | WO 2014/164959 A2 | 10/2014 |
| WO | WO 2015/099175 A1 | 7/2015 |
| WO | WO 2015/106080 A2 | 7/2015 |

(Continued)

OTHER PUBLICATIONS

Hayakawa‡ et al, The Journal of Biological Chemistry; 2007; vol. 282, No. 36, p. 26369-26380.*
Czajkowsky et al, EMBO Molecular Medicine; 2012; vol. 4; pp. 1015-1028.*
Choi et al, Blood. 2009; vol. 114, pp. 3117-3126.*
Ohno, T., et.al., Interleukin-33 in Allergy, Allergy, vol. 67, pp. 1203-1214, 2012.
Mbarik, M., et al., Soluble ST2 and IL-33: Potential markers of endometriosis in the Tunisian population, Immunology Letters, vol. 166, pp. 1-5, 2015.

(Continued)

*Primary Examiner* — Bridget E Bunner
*Assistant Examiner* — Fozia M Hamud
(74) *Attorney, Agent, or Firm* — Knobbe, Martens, Olson & Bear, LLP

(57) ABSTRACT

Based on the identification of IL-33 as an exacerbating factor in endometriosis and adenomyosis uteri, a therapeutic agent for endometriosis and adenomyosis uteri has an IL-33 antagonist, which is capable of inhibiting the function of IL-33. The IL-33 antagonist is useful for treating, preventing or alleviating endometriosis and uterine adenomyosis uteri.

20 Claims, 4 Drawing Sheets
Specification includes a Sequence Listing.

(56) References Cited

FOREIGN PATENT DOCUMENTS

| WO | WO 2016/031932 A1 | 3/2016 |
|---|---|---|
| WO | WO 2016/077366 A1 | 5/2016 |
| WO | WO 2016/140921 A1 | 9/2016 |
| WO | WO 2016/140922 A1 | 9/2016 |
| WO | WO 2016/156440 A1 | 10/2016 |
| WO | WO 2017/062456 A2 | 4/2017 |
| WO | WO 2018/158332 A1 | 9/2018 |

OTHER PUBLICATIONS

Miller, J.E., et al., Pro-inflammatory effects of IL-33 in endometriosis, Reproductive Sciences, Scientific Abstracts, S-113, vol. 24, Supplement 1, p. 270A, 2017.

Miller, J.E., et al., Interleukin-33 Modulates Inflammation in Endometriosis, Reproductive Sciences, Scientific Abstracts, S-106, vol. 25, Supplement 1, p. 287A-288A, 2018.

Miller, J.E., et al., Interleukin-33 Modulates Inflammation in Endometriosis, Scientific Reports, vol. 7, p. 17903-17914, 2017.

Santulli, P., et al., Serum and Peritoneal Interleukin-33 Levels Are Elevated in Deeply Infiltrating Endometriosis, Human Reproduction, vol. 27, No. 7, pp. 2001-2009, 2012.

International Preliminary Report on Patentability, dated Jul. 31, 2019, in International Application No. PCT/JP2018/032494.

International Search Report & Written Opinion, dated Oct. 9, 2018, in International Application No. PCT/JP2018/032494.

Mei et al., Indoleamine 2,3-dioxygenase-1 (ID01) in human endometrial stromal cells induces macrophage tolerance through interleukin-33 in the progression of endometriosis, International Journal of Clinical and Experimental Pathology, vol. 7, No. 6, pp. 2743-2757, 2014.

Akcay et al., "IL-33 exacerbates acute kidney injury," J. Am. Sec. Nephrol., vol. 22, pp. 2057-2067, 2011.

Guabiraba, R., et al., IL-33 Targeting Attenuates Intestinal Mucositis and Enhances Effective Tumour Chemotherapy in Mice, Mucosal Immunology, vol. 7, No. 5, pp. 1079-1093, 2014.

Honda et al., Analytical Tips for Biopharmaceutics Foundation on the Application for Quality Assessment Part 9: Analyzing and engineering protein stabilities, Pharm Tech Japan, vol. 34, No. 5, pp. 885-894, 2018.

Hu et al., "Serum IL-33 as a diagnostic and prognostic marker in non-small cell lung cancer," Asian Pacific Journal of Cancer Prevention, vol. 14, No. 4, pp. 2563-2566, 2013.

Izutsu, K., Lyophilization of Protein Pharmaceuticals, Journal of Pharmaceuticals Science and Technology Japan, vol. 72, No. 6, pp. 353-358, 2012.

Lee, H.Y., et al., Blockade of IL-33/ST2 Ameliorates Airway Inflammation in a Murine Model of Allergic Asthma, Experimental Lung Research, vol. 40, No. 2, pp. 66-76, 2014.

Li, P., et al., IL-33 Neutralization Suppresses Lupus Disease in Lupus-Prone Mice, Inflammation, vol. 37, No. 3, pp. 824-832, 2014.

Liu, X., et al., Structural Insights into the Interaction of IL-33 with its Receptors, PNAS, vol. 110, No. 37, pp. 14918-14923, 2013.

Lloyd et al., "Modelling the human immune response: performance of a 1011 human antibody repertoire against a broad panel of therapeutically relevant antigens", Protein Engineering, Design & Selection vol. 22, No. 3, pp. 159-168, 2009.

Lucchese, G., et al., How a Single Amino Acid Change May Alter the Immunological Information of a Peptide, Frontiers in Bioscience, E4, pp. 1843-1852, Jan. 1, 2012.

Matsuyama et al., "Increased levels of interleukin 33 in sera and synovial fluid from patients with active rheumatoid arthritis," The Journal of Rheumatology, vol. 37, No. 1, pp. 18-25, 2010.

McHedlidze et al., "Interleukin-33-dependent innate lymphoid cells mediate hepatic fibrosis," Immunity, vol. 39, pp. 357-371, Aug. 22, 2013.

Mitzutani, N., et al., Interleukin-33 and alveolar macrophages contribute to the mechanisms underlying the exacerbation of IgE-mediated airway inflammation and remodeling in mice, Immunology, vol. 139, pp. 205-218, 2013.

Nabe, T., Interleukin (IL-)33: New Therapeutic Target for Atopic Diseases Journal of Pharmacological Sciences, vol. 126, No. 2, pp. 85-91, 2014.

Pastorelli et al., "Epithelial-derived IL-33 and its receptor ST2 are dysregulated in ulcerative colitis and in experimental Th1/Th2 driven enteritis," PNAS, vol. 107, No. 17, pp. 8017-8022, Apr. 27, 2010.

Prefontaine et al., "Increased IL-33 expression by epithelial cells in bronchial asthma," J. Allergy Clin. Immunol., Letter to the Editor, vol. 125, No. 3, pp. 752-754, 2010.

Qiu, C., et al., Anti-Interleukin-33 Inhibits Cigarette Smoke-Induced Lung Inflammation in Mice, Immunology, vol. 138, No. 1, pp. 76-82, 2012.

Rankin et al., "IL-33 induces IL-13-dependent cutaneous fibrosis," The Journal of Immunology, pp. 1526-1535, 2010.

Rudikoff, S., et al., Single Amino Acid Substitution Altering Antigen-Binding Specificity, Proc. Natl. Acad. Sci. USA, vol. 79, pp. 1979-1983, Mar. 1982.

Shadie, A.M., et al., Ambient Particulate Matter Includes an Exacerbation of Airway Inflammation in Experimental Asthma: Role of Interleukin-33, Clinical & Experimental Immunology, vol. 177, No. 2, pp. 491-499, 2014.

Suria, "Anaptysbio Announces Development of Novel Anti-IL33 Therapeutic Antibody," AnaptysBio, 1 page, Jan. 10, 2014.

Uchiyama, U., Analytical Tips for Biopharmaceutics Foundation on the Application for Quality Assessment Part 6: Properties of protein solution, Pharm Tech Japan, vol. 34, No. 1, pp. 109-120, 2018.

Xu et al., "IL-33 exacerbates autoantibody-induced arthritis," The Journal of Immunology, pp. 2620-2626, 2010.

Xu, Q., et al., Influenza H1N1 A/Solomon lsland/3/06 Virus Receptor Binding Specificity Correlates with Virus Pathogenicity, Antigenicity, and Immunogenicity in Ferrets, Journal of Virology, vol. 84, No. 10, pp. 4936-4945, May 2010.

Yanaba et al., "Serum IL-33 levels are raised in patients with systemic sclerosis: association with extent of skin sclerosis and severity of pulmonary figrosis," Clin. Rheumatol., vol. 30, pp. 825-830, 2011.

International Search Report dated Mar. 31, 2015 for International Patent Application No. PCT/JP2014/084695 filed Dec. 26, 2014; 4 pages.

Notice of Reasons for Rejection dated Jan. 25, 2022 in Patent Application No. P 2020-219204.

Daugherty et al., Formulation and delivery issues for monoclonal antibody therapeutics, Advanced Drug Delivery Reviews, vol. 58, pp. 686-706, 2006.

Kang et al., Rapid Formulation Development for Monoclonal Antibodies, Bioprocess International, vol. 14, No. 4, pp. 40, 42, 44, and 46, 2016.

Shire, S.J., Chapter 4—Formulation of proteins and monoclonal antibodies (mAbs), Monoclonal Antibodies: Meeting the Challenges in Manufacturing, Formulation, Delivery and Stability of Final Drug Product, pp. 93-120, 2015.

Wang et al., Antibody Structure, Instability, and Formulation, Journal of Pharmaceutical Sciences, vol. 96, No. 1, pp. 1-26, 2007.

European Search Report dated May 6, 2022 for EP Application No. 19860824.2.

* cited by examiner

Lines represent the average ± S.E.M (n=10).
**$P<0.01$ vs WT or control by student's t-test.

*$P<0.05$ control by student's t-test.

Lines represent the average ± S.E.M (n=6-7).
*P<0.05 control by student's t-test.

sST2-Fc

Cont. Fc

Lines represent the average ± S.E.M (n=6).
**$P<0.01$ vs PBS or anti-IL-33 Ab by student's t-test.

Lines represent the average ± S.E.M (n=6).
**$P<0.01$ control by student's t-test.

IL-33 ANTAGONIST-CONTAINING THERAPEUTIC AGENT FOR ENDOMETRIOSIS

PRIORITY AND CROSS REFERENCE TO RELATED APPLICATIONS

This application is the U.S. National Stage Application under 35 U.S.C. § 371 of International Application No. PCT/JP2018/032494, filed Aug. 31, 2018, designating the U.S. and published as WO 2019/045075 A1 on Mar. 7, 2019, which claims the benefit of U.S. Provisional Application No. US 62/552,594, filed Aug. 31, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled SWA018002APCSEQLIST.txt, created and last saved on Feb. 28, 2020, which is 53,370 bytes in size. The information in the Electronic Sequence Listing is incorporated herein by reference in its entirety.

FIELD

The present invention relates to a therapeutic agent for endometriosis comprising an interleukin-33 (IL-33) antagonist as an active ingredient.

BACKGROUND

Endometriosis is a benign (non-malignant) disease in which endometrial tissue proliferates at a site away from the uterine cavity and affects approximately 10% of all women of reproductive age. Endometriosis affects 25-50% of infertile women.

Although there are various theories pertaining to the cause of endometriosis, one cause is thought to be that endometrial cells reach other tissue via menstrual blood causing endometrial tissue to form and proliferate ectopically.

Uterine adenomyosis uteri is a disease in which a lesion resembling endometrium is observed in the myometrium. Although this disease is histologically similar to endometriosis, it is treated as a different disease since the mechanism of occurrence and clinical picture are different. This disease has a peak age of onset in the forties and is associated with the observation of dysmenorrhea, lower abdominal pain, lower back pain, infertility and hypermenorrhea. The typical clinical symptom is menstrual pain and there are many patients who complain of intense pain to a degree that impairs daily life. Patients with adenomyosis uteri may also be complicated with endometriosis and uterine myoma.

Although methods for treating endometriosis or adenomyosis uteri consist of surgery and drug treatment, both of these approaches are symptomatic treatments and a fundamental treatment method for these diseases does not exist. Even in cases in which surgery is selected, it cannot achieve a complete cure due to the need for preserving fertility, and treatment is frequently combined with post-surgical drug therapy to prevent recurrence. Examples of drug therapy include low-dose oral contraceptives, gonadotropin releasing hormone (GnRH) antagonists (such as Leuplin), androgen (such as Danazol), and progesterone (such as Dienogest). However, all of these drugs have adverse side effects due to affecting hormone balance. Namely, Dienogest is known to cause an increase in embryo mortality rate following administration to pregnant rats. Consequently, use during pregnancy is prohibited for all of these drugs. Since many of these drugs are associated with symptoms of pseudomenopause and pseudopregnancy, they have side effects resembling menopausal disorders such as infertility, hot flashes or osteoporosis. Thus, it has been anticipated to develop a preventive agent or therapeutic agent for endometriosis or adenomyosis uteri that is highly safe and does not have an effect on pregnancy.

Interleukin-33 (IL-33) is a cytokine belonging to the Interleukin-1 family that is thought to play a role in an inflammatory condition. IL-33 is constantly expressed within the nuclei of epithelial cells and vascular endothelial cells and functions as an alarmin that is released in conjunction with cell destruction due to tissue damage attributable to infection or physical or chemical stress. Expression of IL-33 is also thought to have a mechanism by which it is increased and secreted in response to stimulation of substances such as lipopolysaccharides. IL-33 released outside from cells binds to IL-33 receptors expressed on cells, thereby an intracellular signal is activated. IL-33 receptors are expressed on various immune system cells and epithelial cells and IL-33 induced intracellular signal transduction occurs in these cells.

IL-33 is thought to induce allergic inflammation (such as asthma, atopic dermatitis, hay fever or anaphylactic shock) by inducing the production of Th2 cytokines (such as IL-4, Il-5, IL-6 or IL-13) from Th2 cells, mast cells, eosinophils, basophils, natural killer (NK) T-cells and group 2 innate lymphoid cells among immune system cells expressing IL-33 receptors (NPL1: Tatsukuni Ohno et al., Allergy, 2012, Vol. 67, p. 1203). Clinical studies have recently been conducted on asthma, atopic dermatitis and peanut allergies as indications for anti-IL-33 antibodies and anti-IL-33 receptor antibodies, which are IL-33 antagonists.

Mbarik, et al. (NPL2: Maruoa Mbarik et al., Immunol. Lett., 2015, Vol. 166, p 1) reported that as a result of analyzing the serum and ascites of endometriosis patients, IL-33 increases in the ascites etc. in endometriosis as the patient's condition (stage) progresses, which make it possible to use as a surrogate marker. IL-33 was reported by. According to the report by Mbarik et al., the concentration of soluble IL-33 receptor (sST2), which functions as an IL-33 antagonist, in ascites is roughly 100 times higher than that of IL-33 and increases together with the progression of endometriosis in the same manner as IL-33. Thus, whether increased expression of IL-33 during endometriosis is a cause of the disease or a result thereof, and what type of pathology it functions in response to are still unclear.

IL-33 antagonists have been reported to be used in the treatment of local fibrosis (PTL1: WO 2016/140921). Although PTL1 mentions endometriosis as one case of local fibrosis, the therapeutic effect against endometriosis is not investigated in the examples. PTL1 merely lists endometriosis as one form of fibrosis and nothing is found regarding the role of IL-33 in endometriosis etc.

CITATION LIST

Patent Literature

PTL1: WO 2016/140921
PTL2: WO 2014/164959
PTL3: WO 2015/099175

Non-Patent Literature

NPL1: Tatsukuni Ohno et al., Allergy, 2012, Vol. 67, p. 1203
NPL2: Maruoa Mbarik et al., Immunol. Lett., 2015, Vol. 166, p. 1

SUMMARY

An agent is sought for treating endometriosis or adenomyosis uteri that is highly safe and does not have an effect on pregnancy.

As a result of conducting extensive studies to solve the aforementioned problems, the inventors of the present invention identified IL-33 as an exacerbating factor of endometriosis or adenomyosis uteri. The inventors of the present invention found that an IL-33 antagonist capable of inhibiting the action of IL-33 is useful for treating, preventing or alleviating endometriosis or adenomyosis uteri, thereby leading to completion of the present invention.

The present invention relates to that indicated below.

[1] A therapeutic agent for endometriosis or adenomyosis uteri comprising an IL-33 antagonist as an active ingredient.

[2] The therapeutic agent described in item 1, which alleviates the pain of endometriosis or adenomyosis uteri.

[3] The therapeutic agent described in item 1 or 2, which inhibits the growth of ectopic endometrial tissue (including cysts) in endometriosis or adenomyosis uteri.

[4] The therapeutic agent described in any of items 1 to 3, which inhibits angiogenesis in ectopic endometrial tissue (including cysts) of endometriosis or adenomyosis uteri.

[5] The therapeutic agent for endometriosis or adenomyosis uteri described in any of items 1 to 4, which inhibits fibrosis or proliferation in ectopic endometrial tissue (including cysts).

[6] The therapeutic agent described in any of items 1 to 5, which inhibits adhesion of ectopic endometrial tissue (including cysts) in endometriosis to various organs.

[7] The therapeutic agent for endometriosis or adenomyosis uteri described in any of items 1 to 6, wherein the IL-33 antagonist is anti-IL-33 antibody, anti-IL-33 receptor antibody or soluble IL-33 receptor.

[8] The therapeutic agent for endometriosis or adenomyosis uteri described in item 7, wherein the IL-33 antibody is A10-1C04, A23-1A05, A25-2C02, A25-3H04 or A26-1F02.

[9] The therapeutic agent for endometriosis or adenomyosis uteri described in item 7, wherein the soluble IL-33 receptor is sST2-Fc.

[10] A therapeutic method for endometriosis or adenomyosis uteri comprising administration of an IL-33 antagonist.

[11] A use of an IL-33 antagonist in the production of a therapeutic agent for endometriosis or adenomyosis uteri.

[12] An IL-33 antagonist for use in the treatment of endometriosis or adenomyosis uteri.

[13] The therapeutic method, use or IL-33 antagonist described in any of items 10 to 12, which alleviates the pain of endometriosis or adenomyosis uteri.

[14] The therapeutic method, use or IL-33 antagonist described in any of items 10 to 12, which inhibits the growth of ectopic endometrial tissue (including cysts) of endometriosis or adenomyosis uteri.

[15] The therapeutic method, use or IL-33 antagonist described in any of items 10 to 12, which inhibits angiogenesis in ectopic endometrial tissue (including cysts) of endometriosis or adenomyosis uteri.

[16] The therapeutic method, use or IL-33 antagonist described in any of items 10 to 12, which inhibits fibrosis or proliferation in ectopic endometrial tissue (including cysts).

[17] The therapeutic method, use or IL-33 antagonist described in any of items 10 to 16, wherein the IL-33 antagonist is anti-IL-33 antibody, anti-IL-33 receptor antibody or soluble IL-33 receptor.

The therapeutic agent for endometriosis or adenomyosis uteri of the present invention has a therapeutic effect on endometriosis or adenomyosis uteri. The therapeutic agent for endometriosis or adenomyosis uteri of the present invention demonstrates at least one action selected from the group consisting of alleviation of pain, inhibition of growth of ectopic endometrial tissue (including cysts), inhibition of angiogenesis in ectopic endometrial tissue (including cysts) and inhibition of fibrosis or proliferation in ectopic endometrial tissue (including cysts) associated with endometriosis or adenomyosis uteri.

DETAILED DESCRIPTION

Figure 1:
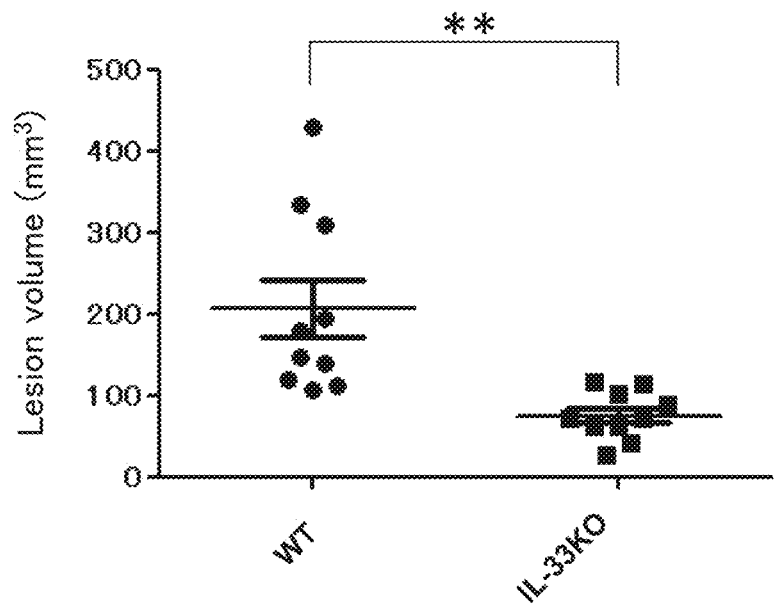
FIG. 1 is a graph indicating inhibition of the growth of a cystic lesion, which is ectopic endometrial tissue, in IL-33 gene knockout mice (IL-33KO) in comparison with wild type control mice (control) in an endometriosis model.

The following provides an explanation of terms used in the present invention in order to facilitate understanding of the present invention.

[IL-33]

IL-33 is a cytokine belonging to the IL-1 family. Human IL-33 is comprised of 270 amino acids as shown in SEQ ID NO: 1 of the sequence listings and the mRNA sequence thereof is shown in SEQ ID NO: 2. IL-33 has a chromatin binding domain on the N-terminal side thereof, has an IL-1-like cytokine domain of a molecular weight of 18 kD that has 12 β strands on the C terminal side thereof, and has cathepsin G cleavage sites at positions 95 and 109, an elastalase cleavage site at position 99 and a caspase cleavage site at position 178. During the course by which cells undergo necrosis, IL-33 is cleaved by enzymes such as elastalase, cathepsin G or proteinase 3 originating in lysosomes resulting in the formation of various fragments containing mature forms of IL-33 such as IL-33 (residue 95 to residue 270) (IL-33 represented with the amino acid sequence from residue 95 to residue 270 from the N terminal in SEQ ID NO:1 of the sequence listings is denoted as "IL-33 (residue 95 to residue 270)", and to apply similarly hereinafter), IL-33 (residue 99 to residue 270), IL-33 (residue 109 to residue 270) or IL-33 (residue 112 to residue 270), and these are thought to function as cytokines. On the other hand, in the case cell death is apoptosis, IL-33 is thought to be cleaved at position 178 by caspase, which has been activated during the course of apoptosis, and form an inactive form of IL-33 such as IL-33 (residue 179 to residue 270).

When released outside from the cell as a cytokine, IL-33 binds with IL-33 receptor and has the function of initiating intracellular signal transduction in the cell expressing said IL-33 receptor. The signal transduction induced by IL-33 non-restrictively includes an NF-κB pathway and MAPKKs pathway, ultimately giving rise to the production of various types of cytokines, chemokines and inflammatory mediators. Examples of cytokines induced by IL-33 include TNF-α, IL-1β, IFN-γ, IL-3, IL-4, IL-5, IL-6 and IL-13, etc. Examples of chemokines induced by IL-33 include CXCL2, CCL2, CCL3, CCL6, CCL17 and CCL24, etc. Examples of inflammatory mediators induced by IL-33 include PGD2 and LTB4, etc. The cytokines, chemokines and inflammatory mediators induced by IL-33 relates to migration of immune system cells, production of cytokines and degranulation, thereby causing inflammation. In the present invention, IL-33 refers to either total length IL-33 or an active fragment thereof in the case of acting by binding to IL-33 receptor to be subsequently described, and may be a derivative or mutant thereof. In the present invention, IL-33 may be human IL-33 or IL-33 of other biological origin. In the present invention, IL-33 is preferably human IL-33 represented by the amino acid sequence of SEQ ID NO: 1 of the sequence listing.

IL-33 receptor bound by IL-33 is composed of a heterodimer of ST2 and IL-1 receptor accessory protein (IL-1RAcP). In an IL-33 receptor, the site that specifically recognizes IL-33 and binds therewith is present in the extracellular region of ST2. IL-33 receptors are expressed in various immune system cells (such as Th2 cells, mast cells, eosinophils, basophils, macrophages, dendritic cells, NK cells, NKT cells, group 2 innate lymphoid cells (natural helper cells), nuocytes or innate helper type 2 (Ih2) cells) and epithelial cells, although not limited thereto.

[IL-33 Antagonist]

In the present invention, an "antagonist" refers to the general term for a substance that acts directly on a desired target, ligand thereof, receptor thereof or gene thereof (including mRNA) and has a neutralizing action on that function. Thus, antagonists not only include substances having an action that directly neutralizes a target function, but also substances having an action that neutralizes a target function indirectly by neutralizing the function of a substance interacting with a target protein or by suppressing gene expression of a target protein. Namely, an "IL-33 antagonist" may be a substance capable of inhibiting any function of IL-33 by binding to IL-33 or a substance capable of inhibiting the function of IL-33 by binding to an IL-33 receptor. Further, antisense and siRNA that suppress gene expression of IL-33 or IL-33 receptor are also included in IL-33 antagonists. IL-33 antagonists include, for example, but not intended to be limited to, anti-IL-33 antibody, anti-IL-33 receptor antibody, soluble IL-33 receptor and aptamers to IL-33 and IL-33 receptor. Anti-IL-33 antibody, anti-IL-33 receptor antibody and aptamers to IL-33 and IL-33 receptor are able to prevent association between IL-33 and IL-33 receptor by binding to IL-33 and IL-33 receptor, which respectively are target molecules thereof. On the other hand, soluble IL-33 receptors are able to prevent association between IL-33 and IL-33 receptors on the cell surface by binding with free IL-33.

[IL-33 Receptor]

Although ST2 gene that encodes a subunit of IL-33 receptor encodes a transmembrane (ST2L) protein, it also encodes a secretory protein that lacks a transmembrane region and intracellular region due to selective splicing. The full length amino acid sequence of human ST2L is represented by SEQ ID NO: 3 of the sequence listings. Among the full length amino acid sequence, an intracellular signal transduction system is activated through binding of IL-33 binding to an IL-33 receptor (heterodimer) formed by association of ST2L with another IL-33 receptor subunit such as IL-1RAcP. IL-33 binds to the extracellular region of ST2L. Thus, ST2L is also simply referred to as an IL-33 receptor.

[Soluble IL-33 Receptor]

The soluble IL-33 receptor in the present invention is a protein that comprises all or a part of the extracellular region of ST2L protein (residue 19 to residue 328 of SEQ ID NO: 3 of the sequence listings), and functions as an IL-33 antagonist as a result of binding with IL-33. The soluble IL-33 receptor may optionally be modified, for example be modified with polyethylene glycol or antibody constant region. In particular, soluble IL-33 receptor having the constant region of an immunoglobulin bound thereto is referred to as sST2-Fc. A preferable example of sST2-Fc is the fusion protein comprised of the extracellular region of human ST2L protein and the constant region of human IgG antibody, which is represented by SEQ ID NO: 5 of the sequence listings.

[Antibody]

In the present invention, the term "antibody" is used in the broadest sense and refers that which includes monoclonal antibody and polyclonal antibody, as long as it exhibits a desired specific bindability. In the present invention, the antibody may be any arbitrary animal antibody such as mouse antibody, human antibody, rat antibody, rabbit antibody, goat antibody or camel antibody.

[Monoclonal Antibody]

Among the antibodies of the present invention, monoclonal antibody refers to an antibody within an antibody population comprised of a single clone (single molecular species) in terms of a designed amino acid sequence. Monoclonal antibodies includes chimeric antibodies, humanized antibodies, human antibodies, multi-specific antibodies and artificial antibodies as well as functionally modified antibodies thereof conjugate antibodies thereof and fragments thereof. The monoclonal antibody of the present invention can be produced using any known technique such as the hybridoma method, phage display method or a genetic engineering technique.

[Chimeric Antibody]

Chimeric antibody refers to an antibody the light chain, heavy chain or both is composed of a variable region of derived from non-human immunoglobulin and a constant region derived from human immunoglobulin.

[Humanized Antibody]

Humanized antibody refers to an antibody comprised of a complementarity determining region derived from non-human immunoglobulin, a variable region comprised of a framework region derived from human immunoglobulin, and a constant region derived from human immunoglobulin.

[Human Antibody]

Human antibody refers to an antibody derived from human immunoglobulin for both the light chain and heavy chain. Human antibody is classified to, depending on the difference in the constant region of the heavy chain, IgG (including IgG1, IgG2, IgG3 and IgG4) having a γ chain heavy chain, IgM having a μ chain heavy chain, IgA (including IgA1 and IgA2) having an α chain heavy chain, IgD having a δ chain heavy chain and IgE having a c chain heavy chain. The light chain comprises either a κ chain or a λ chain in general.

[Multi-Specific Antibody]

Multi-specific antibody refers to an antibody capable of being asymmetrical that has two or more independent antibody recognition sites having two or more different antigen specificities, and examples thereof include bi-specific antibody having two antibody specificities and tri-specific antibody having three antibody specificities. One or more antigens recognized by the multi-specific antibody of the present invention are an IL-33 molecule or IL-33 receptor molecule.

[Artificial Antibody]

Artificial antibodies refers to, for example, protein scaffolds, which although do not have the structure of immunoglobulin, have a function similar to that of immunoglobulin. The Kunitz human serine protease inhibitor domain, human fibronectin extracellular domain, ankyrin and lipocalin are used as protein scaffolds, and a protein scaffold that binds to an epitope in the present invention can be produced if the sequence at the target binding site on the scaffold is modified (Clifford Mintz et al., BioProcess International, 2013, Vol. 11(2), pp 40-48).

[Functionally Modified Antibody]

A functionally modified antibody in the present application refers to an antibody in which function other than the antigen binding function of the antibody, such as a cell killing function, complement activating function or blood half-life, has been adjusted by modifying an amino acid or sugar chain of primarily the constant region of an immunoglobulin.

[Conjugated Antibody]

A conjugated antibody in the present application refers to an antibody in which a functional molecule other than antibody, such as a non-peptidic polymer such as polyethylene glycol (PEG), radioactive substance, toxin, low molecular weight compound, cytokine, albumin or enzyme has been chemically, or using a genetic engineering technique, bound to the antibody.

[Fragment]

An antibody fragment in the present application refers to a protein containing a portion of an antibody that is capable of binding to an antigen. Examples of antibody fragments include Fab fragment, Fv fragment, F(ab)'2 fragment, Fab' fragment and scFv.

These antibody fragments may chemically, or using a genetic engineering technique, bind a functional molecule other than antibody such as a non-peptidic polymer such as polyethylene glycol (PEG), radioactive substance, toxin, low molecular weight compound, cytokine, albumin or enzyme.

[Human Monoclonal Antibody]

Human monoclonal antibody refers to a monoclonal antibody having a variable region and constant region derived from the sequence of an immunoglobulin of a human germ line. These include a monoclonal antibody derived from a transgenic mouse introduced with a human antibody gene and an antibody derived from a human antibody gene library.

[Neutralization]

In the present application, "neutralization" refers to an action capable of inhibiting any target function. Inhibition of the function (biological activity) of IL-33 includes, but is not limited to, the inhibition of the production of IL-33-induced cytokines such as IL-6. An indication of the biological activity of IL-33 can be evaluated by one or more in vitro or in vivo analyses known in the art.

[Complementarity Determining Region]

A complementarity determining region refers to a variable region of an immunoglobulin molecule that forms an antigen binding site, is also referred to as a hypervariable region, and exhibits a large change in the amino acid sequence in particular for each immunoglobulin molecule. A complementarity determining region has three complementarity determining regions for each of the light chain and heavy chain (complementarity determining region 1, complementarity determining region 2 and complementarity determining region 3). In the present application, the complementarity determining region of an immunoglobulin molecule is determined in accordance with the Kabat numbering scheme (Kabat et al., 1987, Sequences of Proteins of Immunological Interest, US Department of Health and Human Services, NIH, USA).

[Aptamer]

An aptamer refers to a nucleic acid molecule that specifically binds with a specific substance, and in the present application, refers to a molecule that functions as an antagonist by binding to IL-33 or IL-33 receptor. An aptamer in the present application may include an artificial nucleic acid molecule other than naturally-occurring nucleic acid molecules.

[Antisense]

Antisense refers to an antisense nucleic acid (such as RNA or DNA) that is capable of hybridizing with the RNA of a target gene and has a function that suppresses expression of gene function. In the present application, antisense refers to a molecule that functions as an antagonist that suppresses expression of a gene by binding to mRNA of IL-33 or IL-33 receptor. Antisense in the present application may also include an artificial nucleic acid molecule other than naturally-occurring nucleic acid molecules.

[siRNA]

Small interfering RNA (siRNA) refers to low molecular weight double-stranded RNA comprised of 15 to 30 base pairs. siRNA is involved in a phenomenon referred to as RNA interference and sequence-specifically suppresses expression of a gene by destroying the mRNA of a target gene. In the present application, siRNA refers to a molecule that functions as an antagonist that suppresses expression of a gene by destroying the mRNA of IL-33 or IL-33 receptor. siRNA in the present application may include an artificial nucleic acid molecule other than naturally-occurring nucleic acid molecules.

[Endometriosis]

Endometriosis is a benign (non-cancerous) disease in which endometrial tissue propagates at a site away from the uterine cavity (ectopically), and examples of such sites include the ovaries, abdominal cavity, peritoneum, Douglas pouch, sigmoid colon, rectum, uterosacral ligament, vagina, vulva, urinary bladder, abdominal wall and navel. Ectopic endometrial tissue may undergo adhesion with various organs. A hematoma of endometrial tissue formed in the ovaries may be referred to as a chocolate cyst. A laparoscopy is performed to make a definitive diagnosis of endometriosis and ectopic endometrial tissue is observed directly. The Re-ASRM classification is used to classify the clinical stage of endometriosis, and classifies endometriosis to Stage 1 to Stage 4 by scoring according to the site of the lesion, whether the lesion is superficial or deep and the degree of adhesion to other organs. The Beecham classification is used to monitor the progress of endometriosis and progress is classified to Stage 1 to Stage 4 corresponding to the progression of the condition.

[Adenomyosis Uteri]

Adenomyosis uteri is a disease in which endometrial tissue is observed in the muscle layer of the uterus, and is classified by MRI diagnosis as focal adenomyosis uteri, which is limited to a portion of the uterus, and diffuse adenomyosis uteri, which extends throughout the uterus.

The following provides an explanation of embodiments of the present invention. The following embodiments are exemplary in order to explain the present invention and the present invention is not limited to these embodiments only.

The present invention relates to a therapeutic agent for endometriosis or adenomyosis uteri comprising an IL-33 antagonist as an active ingredient thereof. The therapeutic agent is able to completely cure, alleviate symptoms or prevent exacerbation by being administered to a patient suffering from endometriosis or adenomyosis uteri. Examples of IL-33 antagonists include anti-IL-33 antibody, anti-IL-33 receptor antibody, IL-33 receptor-binding aptamer and soluble IL-33 receptor.

In another aspect, the present invention relates to a pharmaceutical composition for treating, preventing or alleviating endometriosis or adenomyosis uteri comprising an IL-33 antagonist. In still another aspect, the present invention relates to a method for treating, preventing or alleviating endometriosis or adenomyosis uteri that includes administration of an IL-33 antagonist. The present invention also relates to a use of the IL-33 antagonist of the present invention in order to produce a drug for treating, preventing or alleviating endometriosis or adenomyosis uteri. The present invention also relates to an IL-33 antagonist for use in treating, preventing or alleviating endometriosis or adenomyosis uteri.

Endometriosis is a disease in which endometrial tissue develops at a location other than the endometrium. The disease in which endometrial tissue is present in the muscle layer of the uterus is referred to as adenomyosis uteri. Although this ectopic endometrial tissue undergoes repeated development and bleeding in coordination with the menstrual cycle in the same manner as the endometrium, a hematoma may form since there is no exit as in the case of menstrual blood. A hematoma formed in this manner is referred to as a chocolate cyst. As a result of the formation of a cyst, tissue undergoes fibrosis and can result in the formation of adhesion and induration. When ectopic endometrial tissue ends up adhering to other organs (such as the peritoneum, intestines or ovaries), it causes pain. Adhesion of the fallopian tubes causes infertility. Hormone therapy and resection by a surgical procedure are generally performed for endometriosis. At least one action selected from the group consisting of alleviation of pain associated with endometriosis or adenomyosis uteri, inhibition of the growth of ectopic endometrial tissue (including cysts), inhibition of angiogenesis in ectopic endometrial tissue (including cysts), inhibition of adhesion between various organs and ectopic endometrial tissue (including cysts), and inhibition of fibrosis or cell proliferation is demonstrated by treating, preventing or alleviating endometriosis or adenomyosis uteri.

Patients suffering from endometriosis or adenomyosis uteri have symptoms such as increased menstrual volume and more intense menstrual pain accompanying fluctuations in menstrual cycle. Thus, a therapeutic agent containing an IL-33 antagonist or a pharmaceutical composition for treatment, prevention or alleviation can be administered to subject having changes in symptoms accompanying fluctuations in menstrual cycle and subjects presenting with complaints accompanying fluctuations in menstrual cycle. Such subjects can be distinguished from subjects simply having local fibrosis.

In another aspect of the present invention, the present invention also relates to an alleviator of pain associated with endometriosis or adenomyosis uteri comprising an IL-33 antagonist as an active ingredient, an inhibitor of adhesion of various organs to ectopic endometrial tissue (including cysts) in endometriosis comprising an IL-33 antagonist as an active ingredient, an inhibitor of the growth of ectopic endometrial tissue (including cysts) in endometriosis or adenomyosis uteri comprising an IL-33 antagonist as an active ingredient thereof, an inhibitor of angiogenesis in ectopic endometrial tissue (including cysts) of endometriosis or adenomyosis uteri comprising an IL-33 antagonist as an active ingredient thereof, an inhibitor of fibrosis of endometrial stromal cells in ectopic endometrial tissue (including cysts) of endometriosis or adenomyosis uteri comprising an IL-33 antagonist as an active ingredient thereof, an inhibitor of cell proliferation in endometrial tissue (including cysts) of endometriosis or adenomyosis uteri comprising an IL-33 antagonist as an active ingredient, a superficial endometriosis therapeutic agent comprising an IL-33 antagonist as an active ingredient, a deep endometriosis therapeutic agent comprising an IL-33 antagonist as an active ingredient, a focal adenomyosis uteri therapeutic agent comprising an IL-33 antagonist as an active ingredient thereof, or a diffuse adenomyosis uteri therapeutic agent comprising an IL-33 antagonist as an active ingredient thereof.

The IL-33 antagonist of the present invention preferably alleviates lower back pain, lower abdominal pain or defecation pain during menstruation in endometriosis or adenomyosis uteri patients, or lower back pain, lower abdominal pain or defecation pain at times other than menstruation, and more preferably eliminates that pain.

The IL-33 antagonist of the present invention preferably alleviates pain in the pelvis, ovaries, abdominal cavity, peritoneum, Douglas pouch, sigmoid colon, rectum, uterosacral ligament, vagina, vulva, urinary bladder, abdominal wall and/or navel of endometriosis patients, and more preferably eliminates that pain.

Alleviation of pain by the IL-33 antagonist of the present invention can be evaluated with, for example, the Biberoglu & Behrman scale that scores QOL associated with pain (Biberoglu, K O and Behrman, S J, Am. J. Obstet. Gynecol., 139: 645 (1981)). According to this scale, pain such as pelvic pain, dysmenorrheal pain or coital pain other than during menstruation is evaluated as a subjective symptom.

Alleviation of pain by the IL-33 antagonist of the present invention can be evaluated by a reduction in the number of times an analgesic is taken or the dosage thereof. The analgesic is preferably a non-steroid-based anti-inflammatory analgesic, examples of which include loxoprofen sodium hydrate, diclofenac sodium and aspirin.

The IL-33 antagonist of the present invention preferably inhibits adhesion of ectopic endometrial tissue (including cysts) in the pelvis, ovaries, abdominal cavity, peritoneum, Douglas pouch, sigmoid colon, rectum, uterosacral ligament, vagina, vulva, urinary bladder, abdominal wall and/or navel of endometriosis patients, and more preferably eliminates that adhesion. The IL-33 antagonist of the present invention inhibits adhesion of the uterus and restriction of uterus mobility is preferably alleviated.

The IL-33 antagonist of the present invention preferably inhibits the growth of ectopic endometrial tissue (including cysts) in the pelvis, ovaries, abdominal cavity, peritoneum, Douglas pouch, sigmoid colon, rectum, uterosacral ligament, vagina, vulva, urinary bladder, abdominal wall and/or navel of endometriosis patients, and more preferably reduces that ectopic endometrial tissue (including cysts).

The IL-33 antagonist of the present invention preferably inhibits angiogenesis in ectopic endometrial tissue (including cysts) in the pelvis, ovaries, abdominal cavity, peritoneum, Douglas pouch, sigmoid colon, rectum, uterosacral ligament, vagina, vulva, urinary bladder, abdominal wall and/or navel of endometriosis patients.

The IL-33 antagonist of the present invention preferably inhibits fibrosis or cell proliferation in ectopic endometrial tissue (including cysts) in the pelvis, ovaries, abdominal cavity, peritoneum, Douglas pouch, sigmoid colon, rectum, uterosacral ligament, vagina, vulva, urinary bladder, abdominal wall and/or navel of endometriosis patients.

The IL-33 antagonist of the present invention preferably inhibits the production of cytokines and/or mediators in ectopic endometrial tissue (including cysts) in the pelvis, ovaries, abdominal cavity, peritoneum, Douglas pouch, sigmoid colon, rectum, uterosacral ligament, vagina, vulva, urinary bladder, abdominal wall and/or navel of endometriosis patients, and more preferably inhibits the production of IL-6, TNF-$\alpha$ and/or prostaglandins.

The IL-33 antagonist of the present invention preferably cures patients suffering from Stage 1, Stage 2, Stage 3 and/or Stage 4 endometriosis according to an examination based on the Beecham classification, and preferably cures patients with Stage 1, Stage 2, Stage 3 and/or Stage 4 endometriosis by evaluation of a score determined according to the Re-ASRM classification.

The IL-33 antagonist of the present invention preferably improves QOL associated with endometriosis. Improvement of QOL can be evaluated through interviews using, for example, the Endometriosis Health Profile-30 (EHP-30) (Jones, G. et al., Obstet. Gynecol., 98: 258 (2001)), the EQD-5D (Brooks, R. et al., Health Policy, 37: 53 (1997), or the Endometriosis Treatment Satisfaction Questionnaire (ETSQ) (Deal, L S et al., Qual. Life Res., 19(6), 899 (2010)). Examples of improvement of QOL including improvement of difficulty in standing upright, difficulty in sitting, difficulty in walking, appetite, insomnia, frustration, depression, weepiness, sadness, manic depression, short temperedness, violence, loneliness, loss of confidence and coital difficulty.

A therapeutic agent for endometriosis or adenomyosis uteri that uses an IL-33 antagonist differs from commonly used drug therapy using hormone regulators in that it alleviates infertility and menopausal disorder-like adverse side effects. Thus, the IL-33 antagonist of the present invention is preferably a therapeutic agent for endometriosis or adenomyosis uteri that maintains a fertile state and is free of fetal toxicity during pregnancy, and is preferably a therapeutic agent for endometriosis or adenomyosis uteri that is not accompanied by menopausal disorder-like adverse side effects. Examples of menopausal disorder-like adverse side effects include, but are not limited to, infertility, hot flashes, osteoporosis and depression.

Anti-IL-33 antibody and anti-IL-33 receptor antibody include monoclonal antibodies and polyclonal antibodies. An antibody in the present invention may be an antibody derived from any animal species such as mouse antibody, human antibody, rat antibody, rabbit antibody, goat antibody or camel antibody. The IL-33 antibody and anti-IL-33 receptor antibody of the present invention are preferably monoclonal antibodies and more preferably, the anti-IL-33 antibody and anti-IL-33 receptor antibody of the present invention are monoclonal antibodies that are chimeric antibodies, humanized antibodies or human antibodies.

The anti-IL-33 antibody and anti-IL-33 receptor antibody of the present invention can be acquired by any arbitrary method known in the art. In the case of monoclonal antibodies, antibodies can be acquired using an arbitrary technique such as the hybridoma method, phage display method or a genetic engineering technique.

In the hybridoma method, a hybridoma is produced by fusing B cells acquired from the spleen or lymph nodes of an animal such as a rat or mouse immunized using an immunogen with immortalized cells such as myeloma cells, followed by screening for a hybridoma that produces antibody having a desired bindability and producing that antibody using the screened hybridoma. Human antibody can be acquired by using a mouse introduced with a human antibody gene. In the case of acquiring monoclonal antibody from a hybridoma, a method is employed in which the hybridoma is cultured in accordance with ordinary methods followed by obtaining the antibody in the culture supernatant thereof, or a method is employed in which the hybridoma is allowed to proliferate by administering to a mammal having compatibility therewith followed by obtaining the antibody in ascites thereof. The former method is suitable for obtaining highly pure antibody, while the latter method is suitable for large-volume antibody production. A known technology is used for the technology for producing the monoclonal antibody and this monoclonal antibody can be produced in accordance with the description in, for example, Chapter 2 of Current Protocols in Immunology, Wiley and Sons Inc.

In the phage display method, phages selected from an arbitrary phage antibody library are screened using a target antigen (IL-33 or IL-33 receptor in the present application) followed by selecting a phage having desired bindability for that antigen. Next, the antibody corresponding sequence contained in the phage is isolated or determined and an expression vector containing a nucleic acid molecule encoding a monoclonal antibody is constructed based on the isolated or determined sequence information. A cell line transfected with this expression vector is then cultured to produce monoclonal antibody. Human antibody having a desired bindability can be produced by using a human antibody library for the phage antibody library.

In a genetic engineering technique, antibody having enhanced affinity for antibody and/or a modified function can be produced by introducing a mutation into a sequence corresponding to a complementarity determining region (CDR) or other sequence in a gene sequence encoding an antibody, incorporating that sequence in an expression vector and using this vector to transform a host cell (see, for example, Borrebaeck, C. A. K. and Larrick, J. W., Therapeutic Monoclonal Antibodies, Published in the United Kingdom by MacMillan Publishers, Ltd., 1990).

In the present invention, chimeric antibody, humanized antibody, multi-specific antibody or artificial antibody, for example, can be used for the purpose of lowering xenoantigenicity to humans or adding a different function, and these antibodies can be produced using a known method such as a genetic engineering technique.

Chimeric antibody is obtained by linking DNA encoding the variable region of a non-human immunoglobulin with DNA encoding the constant region of a human immunoglobulin, incorporating this DNA in an expression vector and introducing the expression vector into a host to produce chimeric antibody (see EP 125023, WO 92/19759). Chimeric antibody useful in the present invention can be obtained by using this known method.

Humanized antibody is obtained by linking complementarity determining regions (CDR) derived from a non-human immunoglobulin with DNA encoding the other part of the regions of a human immunoglobulin, incorporating this DNA in an expression vector and introducing the expression vector into a host to produce humanized antibody.

Human antibody is prepared by using, for example, the procedure descried in the Examples provided below. Human antibody can also be prepared by using trioma technology, human B-cell hybridoma technology (Kozbor, et al., 1983, Immunol. Today, 4, p. 72) or EBV hybridoma technology for producing human monoclonal antibody (Cole, et al., 1985, Monoclonal Antibodies and Cancer Therapy, Alan R. Liss, Inc., p. 77). Human antibody can also be produced by preparing a hybridoma by immunizing a transgenic mouse introduced with a human antibody gene with an antigen protein (IL-33 or IL-33 receptor in the present application). Examples of transgenic mice include a HuMab® mouse (Medarex), KMTM mouse (Kirin Pharma), KM(FCγRIIb-KO) mouse and Velocmmune mouse (Regeneron).

Multi-specific antibody can be produced by a genetic engineering technique using the antigen-binding regions of two or more types of monoclonal antibodies. Genetic engineering techniques have already been established in the art. For example, a desired bi-specific antibody can be acquired by using a technology employing DVD-Ig, in which the antigen-binding regions of two types of monoclonal antibodies are linked directly (Wu, et al., Nature Biotechnology, 25(11), 1290 (2007)) or technology employing ART-Ig, in which the heavy chains of two types of antibodies that bind to different antigens are combined by modifying the constant regions of immunoglobulin (Kitazawa, et al., Nature Medicine, 18(10), 1570 (2012)).

Artificial antibody can be acquired for use as artificial antibody that binds to a desired target by using, for example, the 10th unit of the human fibronectin type III domain (FNfin10) and introducing a mutation into the BC, DE and/or FG loop of that unit. In addition to the extracellular domain of fibronectin, peptides such as the Kunitz domain of serine protease inhibitor, ankyrin or lipocalin can be used as artificial antibodies. These artificial antibodies can be produced using a genetic engineering technique by introducing a vector containing a nucleic acid molecule encoding the peptide into *Escherichia coli*, yeast or animal cells, culturing the host cells and purifying from the culture supernatant (PTL4, Clifford Mintz, et al., BioProcesses International, 2013, Vol. 11(2), pp. 40-48).

Artificial antibodies can also be found as low molecular weight peptide molecules that specifically bind to an epitope of the present invention in the similar manner of antibody from random sequence library in which amino acids are randomly combined, instead of using a specific protein as described above or a portion of the amino acid sequence thereof (see, for example, Hipolito, et al., Current Opinion in Chemical Biology, 2012, Vol. 16, 196; Yamagishi, et al., Chemistry & Biology, 2011, Vol. 18, 1562). In addition to genetic engineering techniques, such peptides can also be produced by a chemical synthesis method such as the fluorenyl methyloxy carbonyl method or t-butyloxycarbonyl method.

The monoclonal antibody used in the present invention may be, for example, a conjugated antibody bound with various types of molecules such as a non-peptidic polymer such as polyethylene glycol (PEG), radioactive substance or toxin. Such conjugated antibodies can be obtained by carrying out chemical modification on the resulting antibody. Chemical modification methods have already been established in the art. The monoclonal antibody in the present invention incorporates these conjugated antibodies (King, D. J., Applications and Engineering of Monoclonal Antibodies, 1998, T.J. International Ltd.; Monoclonal Antibody-Based Therapy of Cancer, 1998, Marcel Dekker Inc.; Chari, et al., Cancer Res., 1992, Vol. 152, 127; Liu, et al., Proc. Natl. Acad. Sci. USA, 1996, Vol. 93, 8681).

In the present invention, separate from the whole antibodies described above, fragments of monoclonal antibodies and modified forms thereof may also be used, as long as they have antigen bindability and demonstrate antagonist activity. Examples of antibody fragments include Fab fragments, Fv fragments, F(ab')2 fragments, Fab' fragments and single chain Fv fragments (scFv) in which the Fv of the H chain and L chain are linked with a suitable linker. These antibody fragments may also be linked to a functional molecule other than antibody such as a non-peptidic polymer such as polyethylene glycol (PEG), radioactive substance, toxin, low molecular weight compound, cytokine, albumin or enzyme by means of a chemical technique or genetic engineering technique.

Production systems for producing monoclonal antibody are widely known in the art and can be suitably selected corresponding to the quality of the target formulation. For example, an in vitro or in vivo production system can be used. Examples of in vitro production systems include production systems using eukaryotic cells such as animal cells, plant cells or fungal cells, and production systems using prokaryotic cells such as bacterial cells of *Escherichia coli* or *Bacillus subtilis*. Mammalian cells, for example commonly used cells, such as CHO, COS, myeloma, BHK, HeLa and Vero cells, insect cells or plant cells may be used. Examples of in vivo production systems include production systems using animals and production systems using plants. In the case of using an animal, examples include production systems using mammals and insects. Goats, pigs, sheep, mice or cows, for example, can be used as mammals (Vicki Glaser, Spectrum Biotechnology Applications, 1993). Silkworms, for example, can be used as insects. A tobacco plant, for example, can be used in the case of using a plant.

In the case of producing monoclonal antibody with an in vitro or in vivo production system as described above, DNA encoding the heavy chain (H chain) or light chain (L chain) of an immunoglobulin may be separately incorporated in an expression vectors to simultaneously transform a host, or DNA encoding an H chain and L chain may be incorporated in a single expression vector to transform a host (see WO 94/11523).

The resulting monoclonal antibody can be purified until uniform. Separation and purification methods used with ordinary proteins may be used to separate and purify the monoclonal antibody. For example, monoclonal antibody can be separated and purified by suitably selecting and combining a chromatography column such as that for affinity chromatography, filtration, ultrafiltration, salting out, dialysis, SDS polyacrylamide gel electrophoresis or isoelectric focusing (Antibodies: A Laboratory Manual, Ed Harlow and David Lane, Cold Spring Harbor Laboratory, 1988), although not limited thereto. Examples of columns used for affinity chromatography include a protein A column and protein G column. Examples of columns used a protein A column include Hyper D, POROS and Sepharose F. F. (Amersham Biosciences).

The nucleic acid molecules of the present invention, such as an aptamer, antisense or siRNA, can be synthesized by, for example, the phosphoramidite method using a nucleic acid molecule of a monomer for the material. The phosphoramidite method can be carried out in accordance with a method complying with, for example, the method described in WO 2014/046212. The aptamer of the present invention preferably binds to IL-33 protein (SEQ ID NO: 1 of the sequence listings) or human IL-33 receptor protein (SEQ ID NO: 3 of the sequence listings), and the antisense or siRNA preferably binds to human IL-33 mRNA (SEQ ID NO: 2 of the sequence listings) or human IL-33 receptor mRNA (SEQ ID NO: 4 of the sequence listings). The nucleic acid molecules of the present invention consisting of aptamer, antisense and siRNA may include artificial nucleic acids, and examples of artificial nucleic acids include phosphorothioate (S—PO3)-type oligonucleotides (S-oligo) and 2',4'-bridged nucleic acids (BNA)/2',4'-locked nucleic acids (LNA) (WO 98/39352, WO 2005/021570, WO 2003/068795, WO 2011/052436).

A preferable aspect of the IL-33 antagonist of the present invention is, for example, an aptamer that is able to neutralize the action of IL-33 by binding to human IL-33 receptor, and an example thereof is RBM-009.

The therapeutic agent or pharmaceutical composition comprising the IL-33 antagonist of the present invention may further comprise, a pharmacologically acceptable carrier, diluent or vehicle, in addition to IL-33 antibody, anti-IL-33 receptor antibody or soluble IL-33 receptor, or salts thereof, all of which relates to human IL-33 antagonist as an active ingredient. An active ingredient other than the IL-33 antagonist of the present invention, such as an anti-inflammatory agent or immunosuppressant, may also be contained. Although such a composition is provided as a drug form suitable for parenteral administration or oral administration, parenteral administration is preferable. Examples of parenteral administration, include, but are not limited to, intravenous, intraarterial, subcutaneous, local, intraperitoneal, intramuscular, transnasal, instillation, transdermal, transmucosal, intramedullary, rectal, intramuscular and intravaginal administration.

A suitable drug form can be selected for the therapeutic agent or pharmaceutical composition of the present invention corresponding to the administration route, and any drug form may be used, such as an injection, powder or infusion preparation. From the viewpoint of parenteral administration, an injection, infusion preparation or powder dissolved at the time of use is preferable. These formulations may also contain various adjuvants used for pharmaceuticals, namely carriers and other auxiliary agents such as stabilizers, preservatives, analgesics, emulsifiers and other additives.

The IL-33 antagonist of the present invention can be introduced, for example, by continuous infusion or by bolus administration at an interval of once a day, once a week, once a month or 1 to 7 times in a year. The IL-33 antagonist can be introduced by intravenous, intraperitoneal, subcutaneous, local, transnasal, rectal, intramuscular or intravaginal administration. The preferable dosage protocol includes the maximum dose or dosage frequency that avoids serious adverse side effects. The dosage per administration is generally at least about 0.05 µg/kg of body weight, more generally at least about 0.2 µg/kg, most generally at least about 0.5 µg/kg, typically at least about 1 µg/kg, more typically at least about 10 µg/kg, most typically at least about 100 µg/kg, preferably at least about 0.2 mg/kg, more preferably at least about 1.0 mg/kg, most preferably at least about 2.0 mg/kg, more suitably at least about 10 mg/kg, even more suitably at least about 25 mg/kg, and optically at least about 50 mg/kg.

Examples of preferable aspects of the IL-33 antagonist of the present invention include the human IL-33 monoclonal antibodies of A10-1C04, A23-1A05, A25-2C02, A25-3H04 and A26-1F02. The respective amino acid sequences of the light chains and heavy chains of these monoclonal antibodies are SEQ ID NO: 7 and SEQ ID NO: 8 of the sequence listings (A10-1C04), SEQ ID NO: 9 and SEQ ID NO: 10 (A23-1A05), SEQ ID NO: 11 and SEQ ID NO: 12 (A25-2C02), SEQ ID NO: 13 and SEQ ID NO: 14 (A25-3H04) and SEQ ID NO: 15 and SEQ ID NO: 16 (A26-1F02). The constant regions of these antibodies are preferably constant regions of human antibody, and more preferably the constant region of human IgG1.

Another aspect of the IL-33 antagonist of the present invention is, for example, an antibody that is able to neutralize the action of IL-33 by binding to human IL-33, and examples thereof include etokimab (also referred to as ANB-020), REGN-3500 (also referred to as SAR-440340), MEDI-3506, PF-06817024 and CBP-233.

Another aspect of the IL-33 antagonist of the present invention is, for example, an antibody that is able to neutralize IL-33 by binding to human IL-33 receptor, and examples thereof include RG-6149 (also referred to as AMG-282, MSTT1041A or RO-7187807), GSK-3772847 (also referred to as CNTO-7160) and LY-3375880.

Although soluble IL-33 receptor is a protein having all or a portion of the extracellular region (residue 19 to residue 328) of ST2L of SEQ ID NO: 3 of the sequence listings, an amino acid substitution, deletion or insertion may be contained, as long as the soluble IL-33 receptor demonstrates IL-33 antagonistic action. From the viewpoint of not impairing IL-33 antagonistic action, the number of substituted, deleted or inserted amino acids is preferably one or several, and any arbitrary number of 1 to 9 amino acids can be substituted, deleted or inserted. In another aspect, soluble IL-33 receptor may have identity of at least 80%, more preferably at least 90%, even more preferably at least 95% and still more preferably at least 98% with respect to the amino acid sequence of the extracellular region (residue 19 to residue 328) of ST2L of SEQ ID NO: 3 of the sequence listings, as long as it demonstrates IL-33 antagonistic action. From the viewpoint of improving pharmacokinetics, a constant region of an immunoglobulin and polyethylene glycol, for example, may be fused to the soluble IL-33 receptor. Soluble IL-33 receptor having an antibody constant region fused thereto can be referred to as sST2-Fc. Although the constant region of an immunoglobulin able to be bound may be a constant region derived from any arbitrary species, from the viewpoint of ensuring low antigenicity, a human constant region is preferable. A preferable example of human sST2-Fc is the fusion protein represented by SEQ ID NO: 5 of the sequence listings.

sST2-Fc can form a dimer in the same manner as an immunoglobulin. An amino acid of sST2-Fc may be substituted, deleted or inserted into the original amino acid sequence, such as the amino acid sequence of SEQ ID NO: 5 or 6, as long as it demonstrates IL-33 antagonistic action. From the viewpoint of not impairing IL-33 antagonistic action, the number of substituted, deleted or inserted amino acids is one to several, and any arbitrary number of 1 to 9 amino acids can be substituted, deleted or inserted. In another aspect, sST2-Fc may have identity of at least 80%, more preferably at least 90%, even more preferably at least 95% and still more preferably at least 98% with respect to the amino acid sequence SEQ ID NO: 5 or 6 of the sequence listings, as long as it demonstrates IL-33 antagonistic action. These sST2-Fc preferably maintain the ability to form a dimer.

A soluble IL-33 receptor such as sST2-Fc can be produced using an in vitro production system using a vector containing a nucleic acid that encodes soluble IL-33 receptor protein. Examples of in vitro production systems include production systems using eukaryotic cells such as animal cells, plant cells or fungal cells, and production systems using prokaryotic cells, for example, bacterial cells, such as *Escherichia coli* or *Bacillus subtilis*. Mammalian cells, for example, commonly used cells, such as CHO, COS, myeloma, BHK, HeLa, Vero, 293, NSO, Namaiwa or YB2/0 cells, insect cells or plant cells may be used as animal cells. Soluble IL-33 receptor can be isolated by further purifying the protein produced in this manner.

Although the following provides a more detailed explanation of the present invention through examples thereof, the present invention is not limited to the following examples unless specifically mentioned otherwise. All references mentioned in the present description are incorporated in the present description in their entirety by reference.

Example 1: Effect of IL-33 Gene Deficiency in Endometriosis Model

Transplanted uterus mice administered estrogen were used as an animal model of endometriosis (Ricci, et al., Reprod. Sci., 2011, Vol. 18, p 614). After subjecting wild type, 6-week-old female Balb/c mice (Charles River Laboratories, Japan) or Balb/c-background IL-33 knockout mice (Yasuda, et al., PNAS, 2012, Vol. 130, p 184) (to be denoted as "IL-33KO mice") to inhalation anesthesia with isoflurane (anesthesia maintained at an isoflurane concentration of 3.0% and ambient air flow rate or 300-400), a small incision was made somewhat to the left of the midline of the mice followed by extraction of the left and right uterus from the laparotomy opening in order and excision of the ovaries adhered to the end of the uterus. These mice were subcutaneously injected with an estradiol valerate injection solution (Fuji Pharma) (Estrogen) dissolved to 5 µg/mL with corn oil (Wako Pure Chemical Industries) beneath the skin of the posterior of the neck using a 22G syringe at the rate of 0.5 µg/100 µL/body for 2 weeks (once per week) to produce donor mice and recipient mice. Two weeks later, the donor mice were sacrificed by cervical dislocation and laparotomized followed by excising the uterus. The excised uterus was uniformly cut to a weight of 40 g in a Petri dish. Subsequently, the excised uterus was placed in a 25 mL wide-mouth, round-bottom Spitz tube together with 400 µL of PBS in which was dissolved ampicillin antibiotic (1 mg/mL) followed by finely crushing into the form of a sheet measuring 2 mm on a side with a Cooper scissors. The crushed uterus was aspirated with a 2.5 mL syringe. A small incision was added at the midline of the recipient mice subjected to inhalation anesthesia in the same manner as during ovariectomy, uterine tissue in the syringe was dispersed in the abdominal cavity, and the incision was sutured with 3-0 Monocryl suture. After transplanting the uterine fragment, the recipient mice were subcutaneously further administered estrogen by subcutaneous injection for 2 weeks (once/week). The mice were euthanized and laparotomized two weeks after transplant. The ectopic endometrial tissue (cystic) lesions formed in the abdominal cavity were excised while avoiding damage thereto as much as possible followed by respectively measuring the weight and volume thereof. The volume of the cystic lesions was calculated using V=(4/3)πb2A (b: small diameter, A: large diameter).

As shown in FIG. 1, in the case of using IL-33KO mice for both the donor and recipient, the volume of the cystic lesion decreased significantly in comparison with the case of using wild type mice. Adhesion of the cystic lesions in the IL-33 KO mice to tissue such as the abdominal cavity was inhibited during excision in comparison with cystic lesions of the control mice. The number of blood vessels of the cystic lesions of the IL-33 KO mice appeared to have decreased in comparison with cystic lesions of the control mice. This result indicates that IL-33 is involved in growth of cystic lesions and adhesion to various organs (and adhesion to various organs is a cause of pain) as well as angiogenesis in an endometriosis model, and that inhibition of IL-33 makes it possible to inhibit growth of cystic lesions and their adhesion to various organs (pain) as well as inhibit angiogenesis.

Example 2: Effect of Administration of IL-33 on Endometriosis Model

Figure 2:
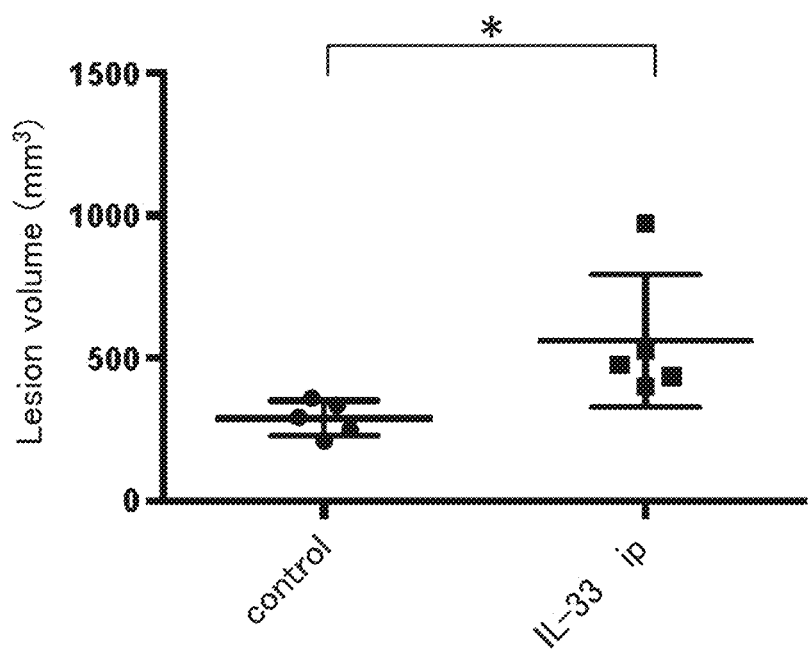
FIG. 2 is a graph indicating promotion of the growth of a cystic lesion, which is ectopic endometrial tissue, in IL-33 dosed mice (IL-33 ip) in comparison with control mice (control) in an endometriosis model.

An endometriosis model was prepared according to the method described in Example 1 using wild-type, 6-week-old female Balb/c mice. The IL-33 dose group was intraperitoneally administered recombinant human IL-33 protein (residue 112 to residue 270) (Kondo, et al., Int. Immunol., 2008, Vol. 20, p 791) dissolved with PBS starting at the time of transplant at the rate of 100 ng/200 µL/body per administration three times per week for 2 weeks for a total of 6 administrations. The mice were euthanized and laparotomized two weeks after transplant followed by excising the cystic lesions that formed in the abdominal cavity and measuring the volume of each lesion. As shown in FIG. 2, the volume of the cystic lesions increased significantly in the IL-33 dose group in comparison with the medium dose group. This result indicates that IL-33 is involved in the growth of cystic lesions. Since the concentration of IL-33 increases in the ascites and serum of endometriosis patients (NPL2), a human IL-33-dosed endometriosis model is thought to be a useful disease model that reflects the pathology of endometriosis.

Example 3: IL-33 Antagonists

Five types of human IL-33 antibodies (A10-1C04, A23-1A05, A25-2C02, A25-3H04 and A26-1F02) along with mouse sST2-Fc, which is a fusion protein of mouse ST2 and human IgG1 constant region, were prepared with recombinant CHO cells (WO 2015/099175). The amino acid sequences thereof are as shown in the table below, and when affinity of the five types of human IL-33 antibodies to human IL-33 protein (residue 112 to residue 270) (ATGen, ILC070) was measured with KinExA, the values of Kd were 100.3 pM for A10-1C04, 195.3 pM for A23-1A05, 700 fM for A25-2C02, 7.7 pM for A25-3H04 and 5.3 pM for A26-1F02.

TABLE 1

| IL-33 Antagonist | Light Chain Sequence | Heavy Chain Sequence |
| --- | --- | --- |
| A10-1C04 | SEQ ID NO: 7 | SEQ ID NO: 8 |
| A23-1A05 | SEQ ID NO: 9 | SEQ ID NO: 10 |
| A25-2C02 | SEQ ID NO: 11 | SEQ ID NO: 12 |
| A25-3H04 | SEQ ID NO: 13 | SEQ ID NO: 14 |

TABLE 1-continued

| IL-33 Antagonist | Light Chain Sequence | Heavy Chain Sequence |
|---|---|---|
| A26-1F02 | SEQ ID NO: 15 | SEQ ID NO: 16 |
| Mouse sST2-Fc | | SEQ ID NO: 6 |

TABLE 2

| | A | B | C | D | E | F | G |
|---|---|---|---|---|---|---|---|
| Control Fc Dose Group | 2 | 3 | 3 | 2 | 2 | 3 | 2.5 |
| Mouse sST2-Fc Dose Group | 1 | 2 | 1 | 3 | 3 | 1 | 1.8 |

Figure 3:
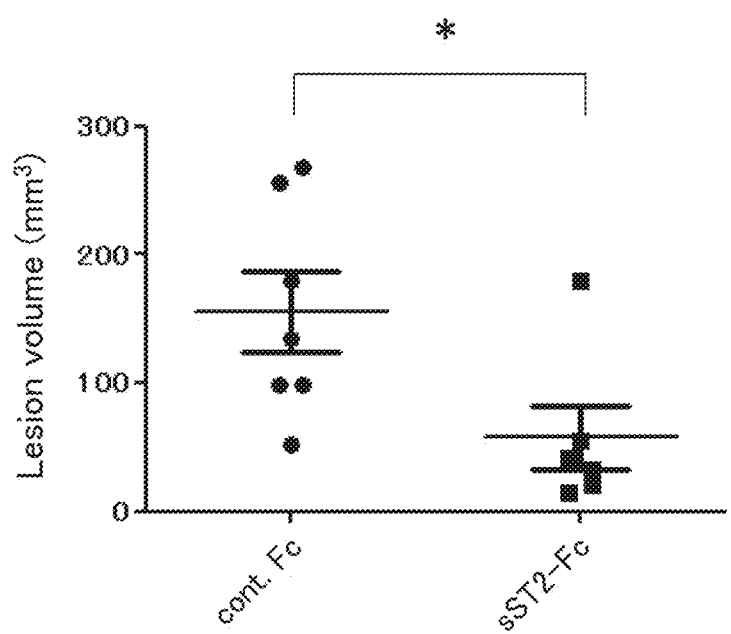
FIG. 3 is a graph indicating inhibition of the growth of a cystic lesion, which is ectopic endometrial tissue, in IL-33 antagonist-dosed mice (sST2-Fc) in comparison with control mice (cont Fc) in an endometriosis model.

Example 4: Effect of IL-33 Antagonist sST2-Fc on Growth of Ectopic Endometrial Tissue Since IL-33 is involved in the proliferation of cystic lesions in an endometriosis model, endometriosis was indicated to be able to be treated by inhibiting IL-33. Endometriosis was therefore treated by administering IL-33 antagonist. The mouse sST2-Fc prepared in Example 3 was used for the IL-33 antagonist. Mouse sST2-Fc was administered intravenously over the course of 2 weeks every 3 days at the rate of 20 mg/kg following transplant of a uterine fragment using an endometriosis model in groups of 6 mice each prepared according to the method indicated in Example 1. A control Fc (InVivoMab Recombinant Human Fc-G1 (Bio X Cell, Cat. No. Be0096) was administered to control mice instead of the mouse sST2-Fc. The mice were euthanized and laparotomized following being treated using mouse sST2-Fc, cystic lesions that formed in the abdominal cavity were excised and the degree of adhesion of the cystic lesions following excision, the volume of the cystic lesions and blood vessels present in the cystic lesions were analyzed. As shown in FIG. 3, the volume of the cystic lesions in the mouse sST2-Fc dose group decreased significantly in comparison with the control Fc dose group. Accompanying this decrease in cystic lesion volume, adhesion of cystic lesions in the mouse sST2-Fc-dosed mice to the peritoneum and other tissue was inhibited at the time of excision in comparison with cystic lesions of the control mice. Cystic lesions in the mouse sST2-Fc-dosed mice demonstrated an apparent decrease in the number of blood vessels in comparison with cystic lesions of the control mice.

On the basis of the above results, endometriosis was able to be treated by administration of mouse sST2-Fc, and growth, adhesion (adhesion to various organs is a cause of pain) and angiogenesis of ectopic endometrial tissue of endometriosis were able to be inhibited.

Figure 4:
FIG. 4 depicts azan-stained images indicating inhibition of fibrosis of a cystic lesion, which is ectopic endometrial tissue, in an IL-33 antagonist-dosed mouse (sST2-Fc) in comparison with a control mouse (cont Fc) in an endometriosis model.
Figure 4:

Example 5: Effect of IL-33 Antagonist sST2-Fc on Fibrosis of Ectopic Endometrial Tissue The cystic lesions excised in Example 4 were fixed with paraformaldehyde followed by embedding in paraffin and preparing paraffin sections having a thickness of 8 μm. Fibrotic tissue was stained blue using a staining solution of Mallory's aniline blue/orange stain G (Muto Pure Chemicals) in accordance with the protocol recommended by Muto Pure Chemicals. The degree of fibrosis was evaluated according to the depth of the blue color of azan staining based on a score of 1 (light) to 3 (dark). As shown in Table 2, fibrosis of the cystic lesions was inhibited in the mouse sST2-Fc dose group in comparison with the control Fc dose group. FIG. 4 depicts average stained images in each group (individual number D of the control Fc dose group and individual number C of the mouse sST2-Fc dose group).

On the basis of the above results, endometriosis is able to be treated by administration of mouse sST2-Fc and fibrosis of ectopic endometrial tissue of endometriosis can be inhibited.

Figure 5:
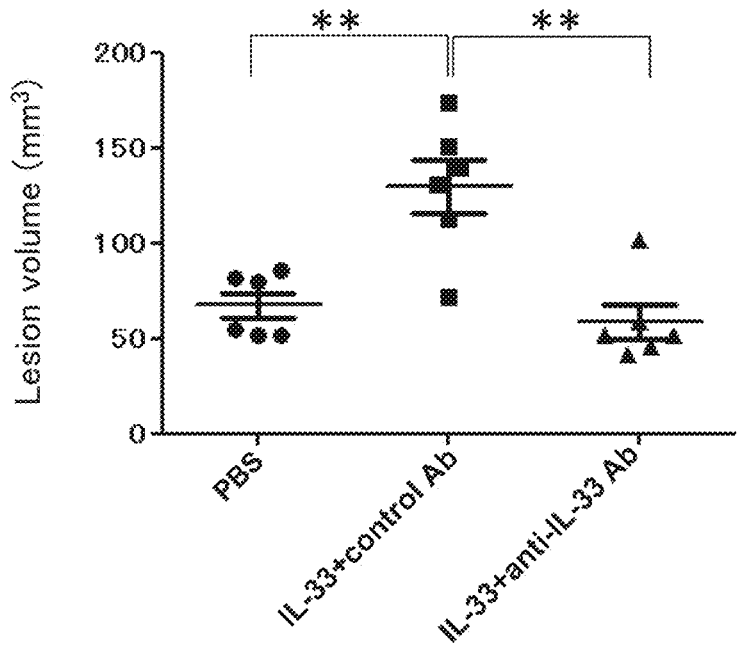
FIG. 5 is a graph indicating inhibition of the growth of a cystic lesion by administration of anti-IL-33 antibody (anti-IL-33) in comparison with control antibody (Control Ab) in an IL-33-dosed endometriosis model.

Example 6: Effect of Anti-IL-33 Monoclonal Antibody on Growth of Ectopic Endometrial Tissue Cystic lesions were shown to increase due to administration of recombinant human IL-33 in a endometriosis model prepared in IL-33 KO mice (Example 2). The effect of the human anti-IL-33 monoclonal antibodies prepared in Example 3 (A10-1C04, A23-1A05, A25-2C02, A25-3H04 and A26-1F02) was investigated using this model. Human anti-IL-33 antibody was administered intravenously every week at the rate of 10 mg/kg after transplanting a uterine fragment using the IL-33-dosed endometriosis model prepared according to the method indicated in Example 2. Control antibody (fully human IgG1 isotype control PC grade (Eureka, Cat. No. ET901)) was administered to the mice of a control group instead of human anti-IL-33 antibody. The mice were euthanized and laparotomized after treating using the human anti-IL-33 antibody, cystic lesions that formed in the abdominal cavity were excised and the degree of adhesion of the cystic lesions following excision, the volume of the cystic lesions and blood vessels present in the cystic lesions were analyzed. As shown in FIG. 5 (showing the results for A10-1C04), the volume of the cystic lesions increased in the human IL-33 dose group in comparison with the PBS dose group, and the volume of the cystic lesions increased significantly even following administration of the control antibody. Increases in volume of the cystic lesions were inhibited significantly by administration of anti-IL-33 antibody. Accompanying a decrease in volume of the cystic lesions, adhesion of cystic lesions in the anti-IL-33 antibody-dosed mice to the peritoneum and other tissue was inhibited at the time of excision in comparison with cystic lesions of the control mice. Cystic lesions in the mouse sST2-Fc-dosed mice demonstrated an apparent decrease in the number of blood vessels in comparison with cystic lesions of the control antibody-dosed mice. Cystic lesions anti-IL-33-dosed mice demonstrated an apparent decrease in the number of blood vessels in comparison with cystic lesions of the control mice.

On the basis of the above results, endometriosis is able to be treated by administration of anti-IL-33 antibody and the growth, adhesion (adhesion to various organs is a cause of pain) and angiogenesis of ectopic endometrial tissue of endometriosis are able to be inhibited.

Figure 6:
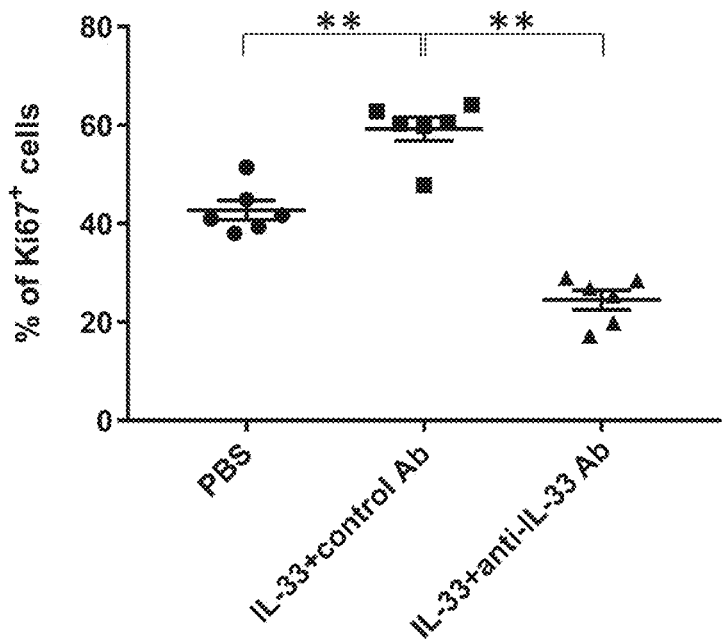
FIG. 6 is a graph indicating inhibition of cell proliferation (percentage of Ki-67-positive cells) in a cystic lesion by administration of anti-IL-33 antibody (Anti-IL-33 Ab) in comparison with control antibody (Control Ab) in an IL-33-dosed endometriosis model.

Example 7: Effect of Anti-IL-33 Monoclonal Antibody on Cell Proliferation of Ectopic Endometrial Tissue The cystic lesions excised in Example 6 were fixed with paraformaldehyde followed by embedding in paraffin and preparing paraffin sections having a thickness of 8 μm. Immunohistostaining of the cell proliferation marker, Ki-67 antigen, was carried out using anti-Ki-67 antibody ("SP6", Abcam, ab16667) and Dako Envision+Dual Link (Agilent, K4063) in accordance with the protocol recommended by Abcam in order to investigate the proliferation of cystic lesions. The Ki-67 positive rate in the cell nuclei per one microscopic field of a section was calculated. The Ki-67 positive rate at three locations per slide was also calculated and the average was determined. As shown in FIG. 6 (indicating the results for A10-1C04), administration of human IL-33 cause an increase in the percentage of Ki-67-positive cells serving as a cell proliferation marker in the cells of cystic lesions associated with endometriosis in comparison with the PBS dose group, and although the increase in the percentage of Ki-67-positive cells increased even following administration of control antibody, that increase was inhibited by administration of anti-IL-33 antibody.

On the basis of the above results, endometriosis is able to be treated by administration of anti-IL-33 antibody and cell proliferation of ectopic endometrial tissue of endometriosis can be inhibited.

Example 8: Effect of Anti-IL-33 Monoclonal Antibody on Pain Associated with Endometriosis Endometriosis and adenomyosis uteri can be treated by administering anti-IL-33 monoclonal antibody to endometriosis and adenomyosis uteri patients. Pain such as pelvic pain, dysmenorrheal pain or coital pain associated with endometriosis and adenomyosis uteri can be alleviated. QOL as related to difficulty in walking and coital pain associated with endometriosis and adenomyosis uteri can be improved.

The therapeutic agent of the present invention having an anti-IL-33 antagonist as an active ingredient thereof can be used as a pharmaceutical composition for treating, preventing or alleviating endometriosis or adenomyosis uteri.

What is claimed is:

1. A method for inhibiting growth of ectopic endometrial tissue of endometriosis or adenomyosis uteri, comprising administration of an IL-33 antagonist.

2. The method according to claim 1, wherein the ectopic endometrial tissue includes cysts.

3. The method according to claim 1, wherein the IL-33 antagonist is an anti-IL-33 antibody, anti-IL-33 receptor antibody or soluble IL-33 receptor.

4. The method according to claim 3, wherein the anti-IL-33 antibody or anti-IL-33 receptor antibody is a monoclonal antibody.

5. The method according to claim 4, wherein the monoclonal antibody is a human monoclonal antibody.

6. The method according to claim 5, wherein a light chain and heavy chain amino acid sequence are respectively selected from the group consisting of SEQ ID NOs: 7 and 8, SEQ ID NOs: 9 and 10, SEQ ID NOs: 11 and 12, SEQ ID NOs: 13 and 14, and SEQ ID NOs: 15 and 16.

7. A method for inhibiting angiogenesis in ectopic endometrial tissue of endometriosis or adenomyosis uteri, comprising administration of an IL-33 antagonist.

8. The method according to claim 7, wherein the ectopic endometrial tissue includes cysts.

9. The method according to claim 7, wherein the IL-33 antagonist is an anti-IL-33 antibody, anti-IL-33 receptor antibody or soluble IL-33 receptor.

10. The method according to claim 9, wherein the anti-IL-33 antibody or anti-IL-33 receptor antibody is a monoclonal antibody.

11. The method according to claim 10, wherein the monoclonal antibody is a human monoclonal antibody.

12. The method according to claim 11, wherein a light chain and heavy chain amino acid sequence are respectively selected from the group consisting of SEQ ID NOs: 7 and 8, SEQ ID NOs: 9 and 10, SEQ ID NOs: 11 and 12, SEQ ID NOs: 13 and 14, and SEQ ID NOs: 15 and 16.

13. A method for inhibiting adhesion of ectopic endometrial tissue in endometriosis to various organs, comprising administration of an IL-33 antagonist.

14. The method according to claim 13, wherein the ectopic endometrial tissue includes cysts.

15. The method according to claim 13, wherein the IL-33 antagonist is an anti-IL-33 antibody, anti-IL-33 receptor antibody or soluble IL-33 receptor.

16. The method according to claim 15, wherein the anti-IL-33 antibody or anti-IL-33 receptor antibody is a monoclonal antibody.

17. The method according to claim 16, wherein the monoclonal antibody is a human monoclonal antibody.

18. The method according to claim 17, wherein a light chain and heavy chain amino acid sequence are respectively selected from the group consisting of SEQ ID NOs: 7 and 8, SEQ ID NOs: 9 and 10, SEQ ID NOs: 11 and 12, SEQ ID NOs: 13 and 14, and SEQ ID NOs: 15 and 16.

19. A method for treating or alleviating endometriosis or adenomoysis uteri, comprising administration of an IL-33 antibody having a light chain and heavy chain amino acid sequence respectively selected from the group consisting of SEQ ID NOs: 7 and 8, SEQ ID NOs: 9 and 10, SEQ ID NOs: 11 and 12, SEQ ID NOs: 13 and 14, and SEQ ID NOs: 15 and 16.

20. The method according to claim 19, wherein a light chain and heavy chain amino acid sequence are respectively SEQ ID NOs: 7 and 8.

* * * * *

UNITED STATES PATENT AND TRADEMARK OFFICE
CERTIFICATE OF CORRECTION

PATENT NO. : 11,492,398 B2
APPLICATION NO. : 16/643502
DATED : November 8, 2022
INVENTOR(S) : Tomohiro Yoshimoto et al.

It is certified that error appears in the above-identified patent and that said Letters Patent is hereby corrected as shown below:

On the Title Page

Page 2, Column 1 (item (56) Other Publications), Line 21, delete "Sec." and insert -- Soc. --.

Page 2, Column 2 (item (56) Other Publications), Line 37, delete "lsland/" and insert -- Island/ --.

Page 2, Column 2 (item (56) Other Publications), Line 43, delete "figrosis,"" and insert -- fibrosis," --.

In the Specification

Column 2, Line 32 (approx.), delete "Il-5," and insert -- IL-5, --.

Column 4, Line 61, delete "12 (3" and insert -- 12 β --.

Column 4, Line 63, delete "elastalase" and insert -- elastase --.

Column 4, Line 66, delete "elastalase," and insert -- elastase, --.

Column 5, Line 28, delete "ofcytokines" and insert -- of cytokines --.

Column 6, Line 52, delete "thereof" and insert -- thereof, --.

Column 10, Line 53, delete "dysmenorrheal" and insert -- dysmenorrhea --.

Column 13, Line 25, delete "Velocmmune" and insert -- VelocImmune --.

Column 13, Line 42, delete "(FNfin10)" and insert -- (FNfn10) --.

Column 13, Line 51, delete "BioProcesses" and insert -- BioProcess --.

Signed and Sealed this
Sixteenth Day of May, 2023

Katherine Kelly Vidal
*Director of the United States Patent and Trademark Office*

Column 13, Line 64, delete "methyloxy" and insert -- methoxy --.

Column 15, Line 20, delete "(S-PO3)-" and insert -- (S-PO)- --.

Column 16, Line 29, delete "MSTTI1041A" and insert -- MSTT1041A --.

Column 20, Line 66, delete "abl 6667)" and insert -- ab16667) --.

Column 22, Line 9, delete "dysmenorrheal" and insert -- dysmenorrhea --.

In the Claims

Column 56, Line 34 (approx.), In Claim 19, delete "adenomoysis" and insert -- adenomyosis --.

```
SEQUENCE LISTING

<160> NUMBER OF SEQ ID NOS: 16

<210> SEQ ID NO 1
<211> LENGTH: 270
<212> TYPE: PRT
<213> ORGANISM: Homo sapiens

<400> SEQUENCE: 1

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
```

```
                    245                 250                 255
Asn Leu Cys Thr Glu Asn Ile Leu Phe Lys Leu Ser Glu Thr
                260                 265                 270

<210> SEQ ID NO 2
<211> LENGTH: 2689
<212> TYPE: DNA
<213> ORGANISM: Homo sapiens

<400> SEQUENCE: 2
agagcugcag cucuucaggg aagaaaucaa aacaagauca caagaauacu gaaaaaugaa       60
gccuaaaaug aaguauucaa ccaacaaaau uccacagca aguggaaga acacagcaag       120 caaagccuug uguucaagc ugggaaaauc ccaacagaag gccaaagaag uugccccau       180 guacuuuaug aagcuccgcu cuggccuuau gauaaaaag gaggccuguu acuuuaggag       240
agaaaccacc aaaaggccuu cacugaaaac agguagaaag cacaaaagac aucugguacu       300
cgcugccugu caacagcagu cuacugugga gugcuuugcc uuugguauau caggggucca       360
gaaauauacu agagcacuuc augauucaag uaucacagga auucaccua uuacagagua       420 ucuugcuucu cuaagcacau acaaugauca auccauuacu uuugcuuugg aggaugaaag       480
uuaugagaua uauguugaag acuugaaaaa agaugaaaag aaagauaagg uguuacugag       540
uuacuaugag ucucaacacc ccucaaauga ucaggugac ggguugaug guaagauguu       600 aaugguaacc cugagucua caaaagacuu cugguugcau gccaacaaca aggaacacuc       660
uguggagcuc auaagugug aaaaaccacu gccagaccag gccuucuuug ccuucauaa       720 uaugcacucc aacuguguuu cauuugaaug caagacugau ccuggagugu uuauaggugu       780
aaaggauaau caucucugcuc ugauuaaagu agacucuucu gagaauuugu guacugaaaa       840
uaucuuguuu aagcucucug aaacuuaguu gauggaaacc ugagucuu ggguugagua       900 cccaaaugcu accacuggag aaggaaugag agauaaagaa agagacaggu gacaucuaag       960
ggaaaugaag agugcuuagc augugguggaa uguuuccau auuauguaua aaauauuuu      1020 uucuaauccu ccaguuauuc uuuuauuucc cucuguauaa cugcaucuuc aauacaagua      1080
ucaguauauu aaauagggua uugguaaaga aacggucaac auucuaaaga gauacagucu      1140
gaccuuuacu uuucucuagu uucaguccag aaagaacuuc auauuuagag cuaaggccac      1200
ugaggaaaga gccauagcuu aagucucucu guagacaggg auccauuuua aagagcuacu      1260
uagagaaaua auuuuccaca guuccaaacg auaggcucaa acacuagagc ugcuaguaaa      1320
aagaagacca gaugcuucac agaauuauca uuuuuucaac uggaauaaaa caccagguuu      1380
guuuguagau gucuuaggca acacucagag cagaucuccc uuacugucag gggauaugga      1440
acuucaaagg cccacaugcc aagccaggua acauaaaugu gugaaaagu aaagauaacu      1500 aaaaauuua gaaaauaaa uccaguauuu guaagugaa uacuucauu ucuaauuguu      1560 uaauuuuuaa aauucugauu uuuauauauu gaguuuaagc aaggcauucu uacacgagga      1620
agugaaguaa auuuuaguuc agacauaaaa uucacuuau uaggaauaug uaacaugcua      1680
aaacuuuuuu uuuuuuaaag aguacugagu cacaacaugu uuagagcau ccaaguacca      1740 uauaauccaa cuaucauggu aaggccagaa aucuucuaac cuaccagagc cuagaugaga      1800
caccgaauua acauuaaaau uucaguaacu gacugucccu caugccaug gccuaccauc      1860 ccuucugacc cuggcuucca gggaccuaug ucuuuaaua cucacuguca cauugggcaa      1920
aguugcuucu aauccuuauu ucccaugugc acaagucuuu uuguauucca gcuuccugau      1980
```

```
aacacugcuu acuguggaau auucauuuga caucugucuc uuuucauuuc uuuuaacuac    2040
caugcccuug auauaucuuu ugcaccugcu gaacuucauu ucuguaucac cugaccucug    2100
gaugccaaaa cguuuauucu gcuuugucug uuguagaauu uuagauaaag cuauuaaugg    2160
caauauuuuu uugcuaaacg uuuuuguuuu uacugucac uagggcaaua aaauuuauac     2220
ucaaccauau aauaacauuu uuuaacuacu aaaggaguag uuuuuauuuu aaagucuuag    2280
caauuucuau uacaacuuuu cuuagacuua acacuuauga uaaaugacua acauaguaac    2340
agaaucuuua ugaauauga ccuuuucuga aaauacauac uuuuacauuu cuacuuuauu     2400
gagaccuauu agauguaagu gcaguagaa uauaagauaa aagaggcuga gaauuaccau     2460
acaaggguau uacaacugua aaacaauuua ucuuuguuuc auuguucugu caauaauugu    2520
uaccaaagag auaaaaauaa aagcagaaug uauaucaucc cacugaaaa acacuaauua     2580 uugacaugug caucugugca auaaacuuaa aaugauuauu aaauaaucaa auauaucuac    2640
auuguuuaua uuauugaaua aaguauauuu uccaaaaaaa aaaaaaaa                 2689
```

<210> SEQ ID NO 3
<211> LENGTH: 556
<212> TYPE: PRT
<213> ORGANISM: Homo sapiens

<400> SEQUENCE: 3

```
Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45

Tyr Tyr Ser Gln Thr Asn Lys Ser Ile Pro Thr Gln Glu Arg Asn Arg
        50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255
```

```
Lys Ile Thr Asp Phe Gly Glu Pro Arg Ile Gln Gln Glu Glu Gly Gln
                260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
                340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
            435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
            515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 4
<211> LENGTH: 2573
<212> TYPE: DNA
<213> ORGANISM: Homo sapiens

<400> SEQUENCE: 4
gaggagggac cuacaaagac uggaaacuau ucuuagcucc gucacugacu ccaaguucau     60
ccccucuguc uuucaguuug guugagauau aggcuacucu ucccaacuca gucuugaaga    120 guauaccaa cugccucaug uggugacc uucacugucg uaugccagug acucaucugg       180
aguaaucuca caacgaguu accaauacuu gcucuugauu gauaaacaga auggggauuu     240
ggaucuuagc aauucucaca auucucaugu auuccacagc agcaaaguuu aguaaacaau    300 caugggccu ggaaaaugag gcuuaauug uaagaugucc uagacaagga aaaccuaguu      360
acaccgugga uugguauuac ucacaaacaa acaaaaguau ucccacucag gaaagaaauc    420
```

```
gugugunugc cucaggccaa cuucugaagu uucuaccagc ugcaguugcu gauucuggua        480
uuuauaccug uauugucaga agucccacau ucaauaggac uggauaugcg aaugucacca        540
uauauaaaaa acaaucagau ugcaauguuc cagauuauuu gaugauuuca acaguaucug        600
gaucagaaaa aaauuccaaa auuuauugac cuaccauuga ccucuacaac uggacagcac        660
cucuugagug guuuaagaau ugucaggcuc uucaaggauc aagguacagg gcgcacaagu        720
cauuuuuggu cauugauaau gugaugacug aggacgcagg ugauuacacc uguaaauuua        780
uacacaauga aauggagcc aauuauagug ugacggcgac caggucccuuc acggucaagg        840 augagcaagg cuuuucucug uuuccaguaa ucggagcccc ugcacaaaau gaaauaaagg        900
aaguggaaau uggaaaaaac gcaaaccuaa cuugcucugc uuguuuugga aaaggcacuc        960
aguucuuggc ugccguccug uggcagcuua auggaacaaa aauuacagac uuuggugaac        1020
caagaauuca acaagaggaa gggcaaaauc aaaguuucag caaugggcug gcuugucuag        1080
acaugguuuu aagaauagcu gacgugaagg aagaggauuu auugcugcag uacgacuguc        1140
uggcccugaa uuugcauggc uugagaaggc acaccguaag acuaaguagg aaaaauccaa        1200
guaaggagug uuucugagac uuugaucacc ugaacuuucu cuagcaagug uaagcagaau        1260 ggagguggu uccaagagau ccaucaagac aaugggaaug gccugugcca uaaaaugugc        1320
uucucuucuu cgggauguug uuugcugucu gaucuuugua gacguuccu guuugcuggg        1380 agcuucucug cugcuuaaau uguucgaccu cccccacucc cuccuaucgu ugguuugucu        1440
agaacacuca gcugcuucu uggucauccu uguuuucuaa cuuuaugaac ucccucugug        1500
ucacuguaug ugaaaggaaa ugcaccaaca accguaaacu gaacguguuc uuugugcuc        1560 uuuuauaacu ugcauuacau guuguaagca uggccguuc uauaccuuuu ucggucaua        1620 augaacacuc auuuguuag cgaggugggu aaaguaaca aaaaggggaa guaucaaacu        1680
acugccauuu cagugagaaa auccuaggug cuacuuuaua auaagacauu guuaggcca        1740 uucuugcauu gauauaaaga aauaccugag acugggugau uuauaugaaa agagguuuaa        1800
uuggcucaca guucgcagg cuguauggga agcauggcgg caucugcuuc uggggacacc        1860
ucaggagcuu uacucauggc agaaggcaaa gcaaggcag gcacuucaca caguaaaagc        1920
aggagcgaga gagaggugcc acacugaaac agccagaucu caugagaagu cacucacuau        1980
ugcaaggaca gcaucaaaga gauggugcua aaccauucau gaugaacuca ccccaugau        2040 ccaaucaccu cccaccaggc uccaccucga auacggggga uuaccauuca gcaugagauu        2100
ugggcaggaa cacagaccca aaccauacca cacacauuau cauuguuaaa cuuuguaaag        2160
uauuuaaggu acauggaaca cacgggaagu cugguagcuc agcccauuuc uuuauugcau        2220
cuguauuuca ccauguaauu cagguaccac guauccagg gagccuuucu uggcccucag        2280
uuugcaguau acacacuuuc caaguacucu uguagcaucc uguuuguauc auagcacugg        2340
ucacauugcc uuaccuaaau cuguuugaca gucugcucaa cacgacugca agcuccauga        2400
gggcagggac aucaucucuu ccaucuuugg guccuuagug caauaccugg cagcuagcca        2460
gugcucagcu aaauauuugu ugacugaaua aaugaaugca caaccaaaaa aaaaaaaaaa        2520
aaaaaaaaaa aaaaaaaaaa aauaaaaaaa aaaaaaaaaa aaaaaaaaaa aaa             2573
```

<210> SEQ ID NO 5
<211> LENGTH: 541
<212> TYPE: PRT
<213> ORGANISM: Artificial Sequence
<220> FEATURE:

<223> OTHER INFORMATION: Fused Protein

<400> SEQUENCE: 5

```
Lys Phe Ser Lys Gln Ser Trp Gly Leu Glu Asn Glu Ala Leu Ile Val
1               5                   10                  15
Arg Cys Pro Arg Gln Gly Lys Pro Ser Tyr Thr Val Asp Trp Tyr Tyr
            20                  25                  30
Ser Gln Thr Asn Lys Ser Ile Pro Thr Gln Glu Arg Asn Arg Val Phe
        35                  40                  45
Ala Ser Gly Gln Leu Leu Lys Phe Leu Pro Ala Ala Val Ala Asp Ser
    50                  55                  60
Gly Ile Tyr Thr Cys Ile Val Arg Ser Pro Thr Phe Asn Arg Thr Gly
65                  70                  75                  80
Tyr Ala Asn Val Thr Ile Tyr Lys Lys Gln Ser Asp Cys Asn Val Pro
                85                  90                  95
Asp Tyr Leu Met Tyr Ser Thr Val Ser Gly Ser Glu Lys Asn Ser Lys
            100                 105                 110
Ile Tyr Cys Pro Thr Ile Asp Leu Tyr Asn Trp Thr Ala Pro Leu Glu
        115                 120                 125
Trp Phe Lys Asn Cys Gln Ala Leu Gln Gly Ser Arg Tyr Arg Ala His
    130                 135                 140
Lys Ser Phe Leu Val Ile Asp Asn Val Met Thr Glu Asp Ala Gly Asp
145                 150                 155                 160
Tyr Thr Cys Lys Phe Ile His Asn Glu Asn Gly Ala Asn Tyr Ser Val
                165                 170                 175
Thr Ala Thr Arg Ser Phe Thr Val Lys Asp Glu Gln Gly Phe Ser Leu
            180                 185                 190
Phe Pro Val Ile Gly Ala Pro Ala Gln Asn Glu Ile Lys Glu Val Glu
        195                 200                 205
Ile Gly Lys Asn Ala Asn Leu Thr Cys Ser Ala Cys Phe Gly Lys Gly
    210                 215                 220
Thr Gln Phe Leu Ala Ala Val Leu Trp Gln Leu Asn Gly Thr Lys Ile
225                 230                 235                 240
Thr Asp Phe Gly Glu Pro Arg Ile Gln Gln Glu Gly Gln Asn Gln
                245                 250                 255
Ser Phe Ser Asn Gly Leu Ala Cys Leu Asp Met Val Leu Arg Ile Ala
            260                 265                 270
Asp Val Lys Glu Glu Asp Leu Leu Leu Gln Tyr Asp Cys Leu Ala Leu
        275                 280                 285
Asn Leu His Gly Leu Arg Arg His Thr Val Arg Leu Ser Arg Lys Asn
    290                 295                 300
Pro Ile Asp His His Ser Pro Lys Ser Cys Asp Lys Thr His Thr Cys
305                 310                 315                 320
Pro Pro Cys Pro Ala Pro Glu Leu Leu Gly Gly Pro Ser Val Phe Leu
                325                 330                 335
Phe Pro Pro Lys Pro Lys Asp Thr Leu Met Ile Ser Arg Thr Pro Glu
            340                 345                 350
Val Thr Cys Val Val Val Asp Val Ser His Glu Asp Pro Glu Val Lys
        355                 360                 365
Phe Asn Trp Tyr Val Asp Gly Val Glu Val His Asn Ala Lys Thr Lys
    370                 375                 380
Pro Arg Glu Glu Gln Tyr Asn Ser Thr Tyr Arg Val Val Ser Val Leu
385                 390                 395                 400
```

Thr Val Leu His Gln Asp Trp Leu Asn Gly Lys Glu Tyr Lys Cys Lys
            405                 410                 415

Val Ser Asn Lys Ala Leu Pro Ala Pro Ile Glu Lys Thr Ile Ser Lys
        420                 425                 430

Ala Lys Gly Gln Pro Arg Glu Pro Gln Val Tyr Thr Leu Pro Pro Ser
    435                 440                 445

Arg Glu Glu Met Thr Lys Asn Gln Val Ser Leu Thr Cys Leu Val Lys
450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
            485                 490                 495

Ser Phe Phe Leu Tyr Ser Lys Leu Thr Val Asp Lys Ser Arg Trp Gln
        500                 505                 510

Gln Gly Asn Val Phe Ser Cys Ser Val Met His Glu Ala Leu His Asn
    515                 520                 525

His Tyr Thr Gln Lys Ser Leu Ser Leu Ser Pro Gly Lys
530                 535                 540

<210> SEQ ID NO 6
<211> LENGTH: 537
<212> TYPE: PRT
<213> ORGANISM: Artificial Sequence
<220> FEATURE:
<223> OTHER INFORMATION: Fused Protein

<400> SEQUENCE: 6

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
            20                  25                  30

Thr Asn Glu Ser Ile Pro Thr Gln Lys Arg Asn Arg Ile Phe Val Ser
        35                  40                  45

Arg Asp Arg Leu Lys Phe Leu Pro Ala Arg Val Glu Asp Ser Gly Ile
    50                  55                  60

Tyr Ala Cys Val Ile Arg Ser Pro Asn Leu Asn Lys Thr Gly Tyr Leu
65                  70                  75                  80

Asn Val Thr Ile His Lys Lys Pro Pro Ser Cys Asn Ile Pro Asp Tyr
                85                  90                  95

Leu Met Tyr Ser Thr Val Arg Gly Ser Asp Lys Asn Phe Lys Ile Thr
            100                 105                 110

Cys Pro Thr Ile Asp Leu Tyr Asn Trp Thr Ala Pro Val Gln Trp Phe
        115                 120                 125

Lys Asn Cys Lys Ala Leu Gln Glu Pro Arg Phe Arg Ala His Arg Ser
    130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205

Pro Ala Ser Ile Ala Cys Ser Ala Cys Phe Gly Lys Gly Ser His Phe
    210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Gly Arg Asn Glu Ser Ser Ser
            245                 250                 255

Asn Asp Met Asp Cys Leu Thr Ser Val Leu Arg Ile Thr Gly Val Thr
            260                 265                 270

Glu Lys Asp Leu Ser Leu Glu Tyr Asp Cys Leu Ala Leu Asn Leu His
            275                 280                 285

Gly Met Ile Arg His Thr Ile Arg Leu Arg Arg Lys Gln Pro Ile Asp
            290                 295                 300

His Arg Pro Lys Ser Cys Asp Lys Thr His Thr Cys Pro Pro Cys Pro
305                 310                 315                 320

Ala Pro Glu Leu Leu Gly Gly Pro Ser Val Phe Leu Phe Pro Pro Lys
            325                 330                 335

Pro Lys Asp Thr Leu Met Ile Ser Arg Thr Pro Glu Val Thr Cys Val
            340                 345                 350

Val Val Asp Val Ser His Glu Asp Pro Glu Val Lys Phe Asn Trp Tyr
            355                 360                 365

Val Asp Gly Val Glu Val His Asn Ala Lys Thr Lys Pro Arg Glu Glu
370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
            405                 410                 415

Ala Leu Pro Ala Pro Ile Glu Lys Thr Ile Ser Lys Ala Lys Gly Gln
            420                 425                 430

Pro Arg Glu Pro Gln Val Tyr Thr Leu Pro Pro Ser Arg Glu Glu Met
            435                 440                 445

Thr Lys Asn Gln Val Ser Leu Thr Cys Leu Val Lys Gly Phe Tyr Pro
            450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
            485                 490                 495

Tyr Ser Lys Leu Thr Val Asp Lys Ser Arg Trp Gln Gln Gly Asn Val
            500                 505                 510

Phe Ser Cys Ser Val Met His Glu Ala Leu His Asn His Tyr Thr Gln
            515                 520                 525

Lys Ser Leu Ser Leu Ser Pro Gly Lys
530                 535

<210> SEQ ID NO 7
<211> LENGTH: 215
<212> TYPE: PRT
<213> ORGANISM: Artificial Sequence
<220> FEATURE:
<223> OTHER INFORMATION: Light Chain of Antibody

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Val
            20                  25                  30

Tyr Asp Val His Trp Tyr Gln Gln Leu Pro Gly Thr Ala Pro Lys Leu
            35                  40                  45

```
Leu Ile Tyr Arg Asn Asn Gln Arg Pro Ser Gly Val Pro Asp Arg Phe
         50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Gln Thr Tyr Asp Ser Ser
                 85                  90                  95

Arg Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
210                 215

<210> SEQ ID NO 8
<211> LENGTH: 446
<212> TYPE: PRT
<213> ORGANISM: Artificial Sequence
<220> FEATURE:
<223> OTHER INFORMATION: Heavy Chain of Antibody

<400> SEQUENCE: 8

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ser Ile Ser Arg Tyr Ser Ser Tyr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ile Gly Gly Met Asp Val Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 9
<211> LENGTH: 216
<212> TYPE: PRT
<213> ORGANISM: Artificial Sequence
<220> FEATURE:
<223> OTHER INFORMATION: Light Chain of Antibody

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Ala Ser Asn Met Arg Val Ile Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Gln
                85                  90                  95

Lys Ala Leu Val Phe Gly Gly Gly Thr Lys Leu Thr Val Leu Gly Gln
            100                 105                 110

```
Pro Lys Ala Ala Pro Ser Val Thr Leu Phe Pro Pro Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 10
<211> LENGTH: 449
<212> TYPE: PRT
<213> ORGANISM: Artificial Sequence
<220> FEATURE:
<223> OTHER INFORMATION: Heavy Chain of Antibody

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Arg Tyr His Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Asn Ala Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 11
<211> LENGTH: 216
<212> TYPE: PRT
<213> ORGANISM: Artificial Sequence
<220> FEATURE:
<223> OTHER INFORMATION: Light Chain of Antibody

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Ala Val Asn Trp Tyr Gln Gln Leu Pro Gly Thr Ala Pro Lys Leu Leu
            35                  40                  45

Ile Tyr Ala Ser Asn Met Arg Val Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Trp Ala Trp Asp Asp Ser Gln
            85                  90                  95

Lys Val Gly Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
```

```
                    165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 12
<211> LENGTH: 449
<212> TYPE: PRT
<213> ORGANISM: Artificial Sequence
<220> FEATURE:
<223> OTHER INFORMATION: Heavy Chain of Antibody

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg Asn Asn Ala Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
            325                 330                 335

Leu Pro Pro Ser Arg Asp Glu Leu Thr Lys Asn Gln Val Ser Leu Thr
        340                 345                 350

Cys Leu Val Lys Gly Phe Tyr Pro Ser Asp Ile Ala Val Glu Trp Glu
    355                 360                 365

Ser Asn Gly Gln Pro Glu Asn Asn Tyr Lys Thr Thr Pro Pro Val Leu
370                 375                 380

Asp Ser Asp Gly Ser Phe Phe Leu Tyr Ser Lys Leu Thr Val Asp Lys
        385                 390                 395         400

Ser Arg Trp Gln Gln Gly Asn Val Phe Ser Cys Ser Val Met His Glu
    405                 410                 415

Ala Leu His Asn His Tyr Thr Gln Lys Ser Leu Ser Leu Ser Pro Gly
        420                 425                 430

Lys
435                 440                 445

<210> SEQ ID NO 13
<211> LENGTH: 216
<212> TYPE: PRT
<213> ORGANISM: Artificial Sequence
<220> FEATURE:
<223> OTHER INFORMATION: Light Chain of Antibody

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Gln
            85                  90                  95

Lys Val Val Val Phe Gly Gly Gly Thr Lys Leu Thr Val Leu Gly Gln
        100                 105                 110

Pro Lys Ala Ala Pro Ser Val Thr Leu Phe Pro Pro Ser Ser Glu Glu
    115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
        180                 185                 190

Arg Ser Tyr Ser Cys Gln Val Thr His Glu Gly Ser Thr Val Glu Lys
    195                 200                 205

Thr Val Ala Pro Thr Glu Cys Ser
210                 215

<210> SEQ ID NO 14
<211> LENGTH: 449
<212> TYPE: PRT
<213> ORGANISM: Artificial Sequence
<220> FEATURE:
<223> OTHER INFORMATION: Heavy Chain of Antibody

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Tyr Met His Trp Val Arg Gln Ala Pro Gly Lys Gly Leu Glu Trp Val
        35                  40                  45

Ser Ser Ile Ser Ala Gln Ser Ser His Ile Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg Gln Asn Ala Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 15
<211> LENGTH: 216
<212> TYPE: PRT
<213> ORGANISM: Artificial Sequence
<220> FEATURE:
<223> OTHER INFORMATION: Light Chain of Antibody

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Ser Asn Met Arg Arg Pro Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Glu Ala Trp Asp Asp Ser Gln
                85                  90                  95

Lys Ala Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 16
<211> LENGTH: 449
<212> TYPE: PRT
<213> ORGANISM: Artificial Sequence
<220> FEATURE:
<223> OTHER INFORMATION: Heavy Chain of Antibody

<400> SEQUENCE: 16
```

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met His Trp Val Arg Gln Ala Pro Gly Lys Gly Leu Glu Trp Val
        35                  40                  45

Ser Ser Ile Ser Ala Arg Ser Ser Tyr Leu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Thr Arg His Val Ala Phe Asp Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```